(12) United States Patent
Kyomoto et al.

(10) Patent No.: US 9,700,651 B2
(45) Date of Patent: Jul. 11, 2017

(54) BEARING MATERIAL AND METHOD OF PRODUCING THE SAME

(71) Applicant: KYOCERA Medical Corporation, Osaka-shi, Osaka (JP)

(72) Inventors: Masayuki Kyomoto, Osaka (JP); Shihori Yamane, Osaka (JP); Kenichi Saiga, Osaka (JP)

(73) Assignee: KYOCERA MEDICAL CORPORATION, Osaka-Shi, Osaka (JP)

( * ) Notice: Subject to any disclaimer, the term of this patent is extended or adjusted under 35 U.S.C. 154(b) by 1 day.

(21) Appl. No.: 14/404,248

(22) PCT Filed: May 30, 2013

(86) PCT No.: PCT/JP2013/065074
§ 371 (c)(1),
(2) Date: Nov. 26, 2014

(87) PCT Pub. No.: WO2013/180228
PCT Pub. Date: Dec. 5, 2013

(65) Prior Publication Data
US 2015/0141545 A1    May 21, 2015

(30) Foreign Application Priority Data

May 31, 2012 (JP) .................................. 2012-124969
Dec. 27, 2012 (JP) .................................. 2012-285879
Feb. 28, 2013 (JP) .................................. 2013-039425

(51) Int. Cl.
*A61L 27/16* (2006.01)
*A61L 27/34* (2006.01)
(Continued)

(52) U.S. Cl.
CPC ................ *A61L 27/16* (2013.01); *A61F 2/30* (2013.01); *A61L 27/34* (2013.01); *A61L 27/505* (2013.01);
(Continued)

(58) Field of Classification Search
CPC ....................................... A61L 27/16
See application file for complete search history.

(56) References Cited

U.S. PATENT DOCUMENTS 6,228,900 B1    5/2001  Shen et al.
2003/0212161 A1  11/2003  McKellop et al.
(Continued)

FOREIGN PATENT DOCUMENTS

CN    102089333 A    6/2011
JP    2000/514481 A   10/2000
(Continued)

OTHER PUBLICATIONS

Electrasol™ MSDS, Reckitt Benckiser, Mar. 18, 2004.*
(Continued)

*Primary Examiner* — Michael Pepitone
(74) *Attorney, Agent, or Firm* — Volpe and Koenig, P.C.

(57) ABSTRACT

An object of the present invention is to provide a method of producing a bearing material having excellent wear-resistance and oxidation resistance. The method of producing a bearing material 10 according to the present invention comprises molding a substrate 12 containing a radical scavenger and a polymer material; washing at least a part 16 of the substrate 12 with a washing liquid; and grafting a polymer chain having a phosphorylcholine group from at least the part 16 of the surface after washing so as to form a polymer film 30 on at least the part of the surface.

14 Claims, 23 Drawing Sheets

(51) Int. Cl.
*A61F 2/30* (2006.01)
*A61L 27/50* (2006.01)
*C08J 3/28* (2006.01)

(52) U.S. Cl.
CPC ....... *C08J 3/28* (2013.01); *A61F 2002/30685* (2013.01); *A61F 2002/30934* (2013.01); *A61L 2400/10* (2013.01); *A61L 2430/24* (2013.01); *C08J 2323/06* (2013.01)

(56) References Cited

U.S. PATENT DOCUMENTS

| | | |
|---|---|---|
| 2004/0243249 A1 | 12/2004 | Ishihara et al. |
| 2009/0306781 A1 | 12/2009 | Kyomoto et al. |
| 2011/0109017 A1* | 5/2011 | Muratoglu .............. A61L 27/16 264/488 |
| 2011/0116968 A1 | 5/2011 | Brunner et al. |
| 2012/0022665 A1 | 1/2012 | Kyomoto et al. |
| 2012/0197407 A1 | 8/2012 | Kyomoto et al. |
| 2012/0197413 A1 | 8/2012 | Kyomoto et al. |

FOREIGN PATENT DOCUMENTS

| | | |
|---|---|---|
| JP | 2003/310649 A | 11/2003 |
| JP | 4256096 B2 | 4/2009 |
| JP | 4963838 B2 | 6/2012 |
| JP | 5028080 B2 | 9/2012 |
| WO | 2007/091521 A1 | 8/2007 |
| WO | 2009/044816 A1 | 4/2009 |
| WO | 2010/074238 A1 | 7/2010 |
| WO | 2011/021642 A1 | 2/2011 |

OTHER PUBLICATIONS

Ishihara, K.; Iwasaki, Y.; Ebihara, S.; Shindo, Y.; Nakabayashi, N. Colloids Surf. B. 2000, 18, 325.*

International Search Report, PCT/JP2013/065074, Jun. 13, 2013, 2 pgs.

Extended European Search Report, European Patent Application No. 13797265.9, Jan. 29, 2016, 10 pgs.

Moro, T., et al., "Surface grafting of biocompatible phospholipid polymer MPC provides wear resistance of tibial Dolyethylene insert in artificial knee joints," Osteoarthritis and Cartilage, Bailliere Tindall, London, GB, vol. 18, No. 9, Sep. 1, 2010, (Sep. 1, 2010), pp. 1174-1182 [retrieved on Jul. 13, 2010].

Moro, T., et al., "Surface grafting of artificial joints with a biocompatible polymer for preventing periprosthetic osteolysis," Nature Materials, Nature Publishing Group, London, GB, vol. 3, Jan. 1, 2004 (Jan. 1, 2004), pp. 329-836.

Enrique Gomez-Barrena, et al., "Update on UHMWPE research from the bench to the bedside," ACTA Orthopaedica, vol. 79, No. 6, Jan. 1, 2008 (Jan. 1, 2008), pp. 832-840.

Chinese Office Action with English concise explanation, Chinese Patent Application No. 201380027464.5, Aug. 4, 2015, 21 pgs.

\* cited by examiner

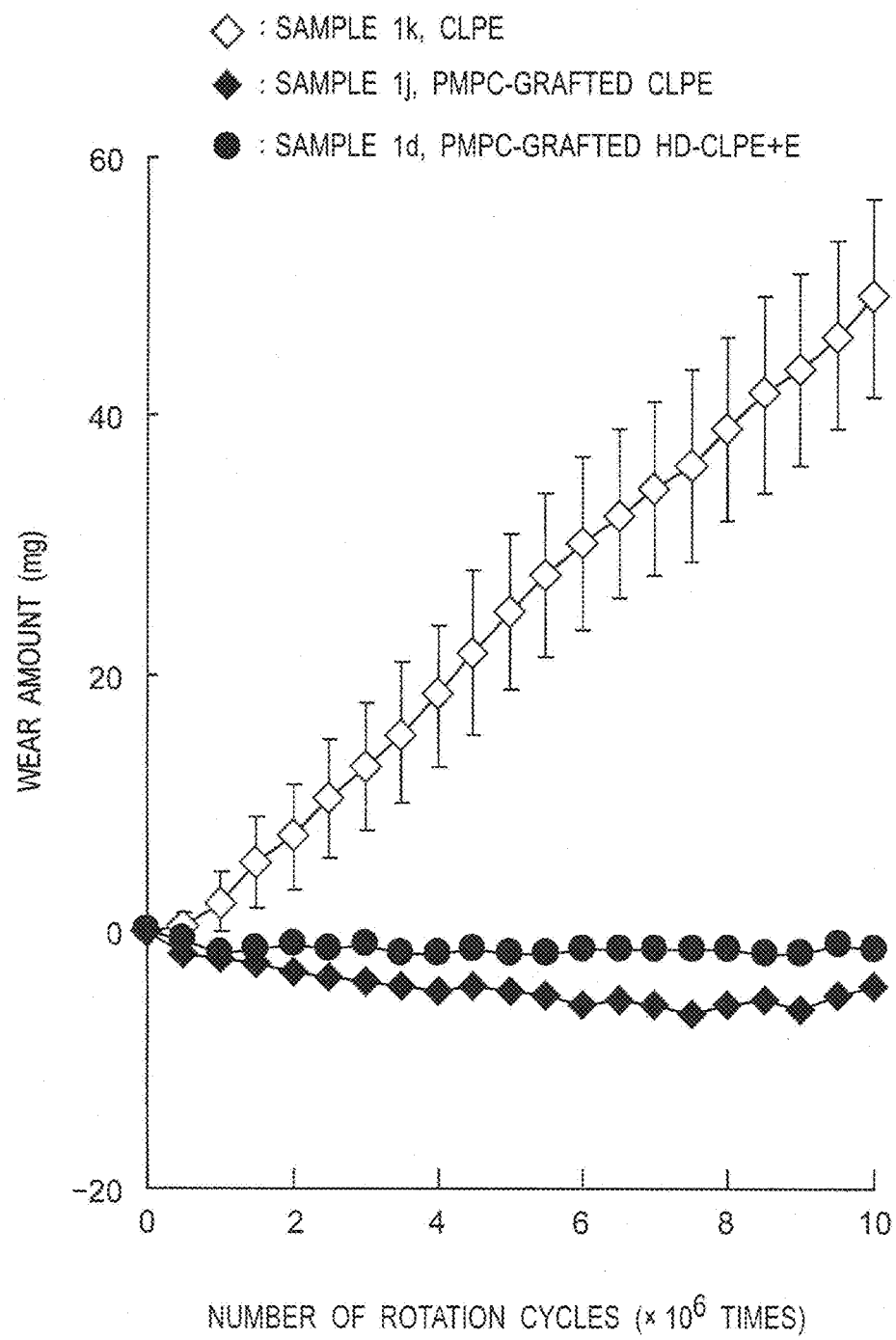

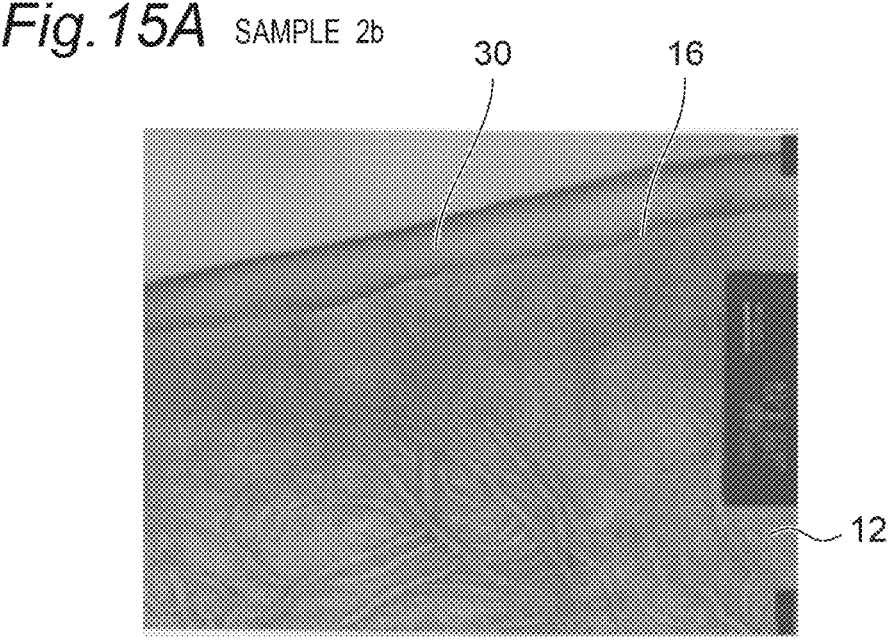
*Fig. 15A* SAMPLE 2b
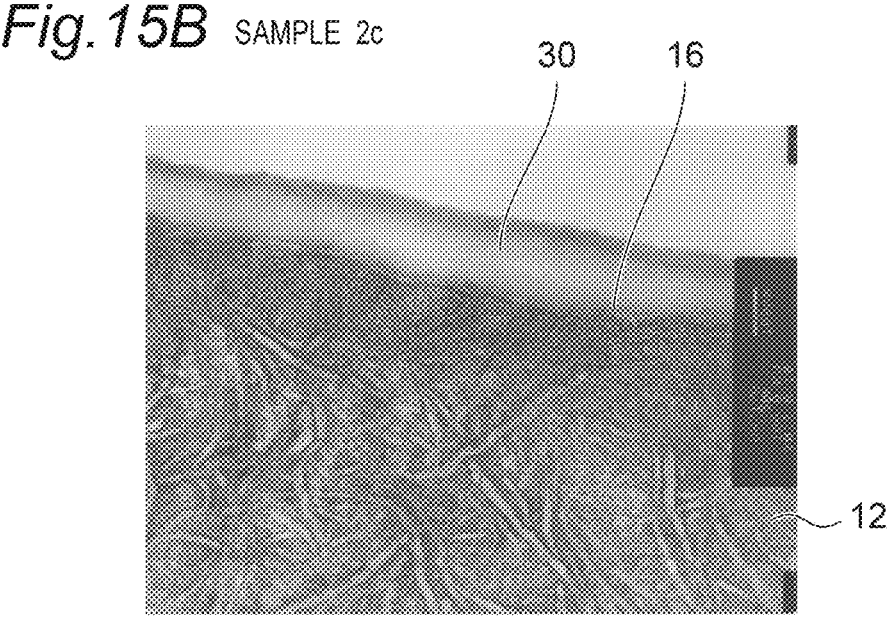
*Fig. 15B* SAMPLE 2c

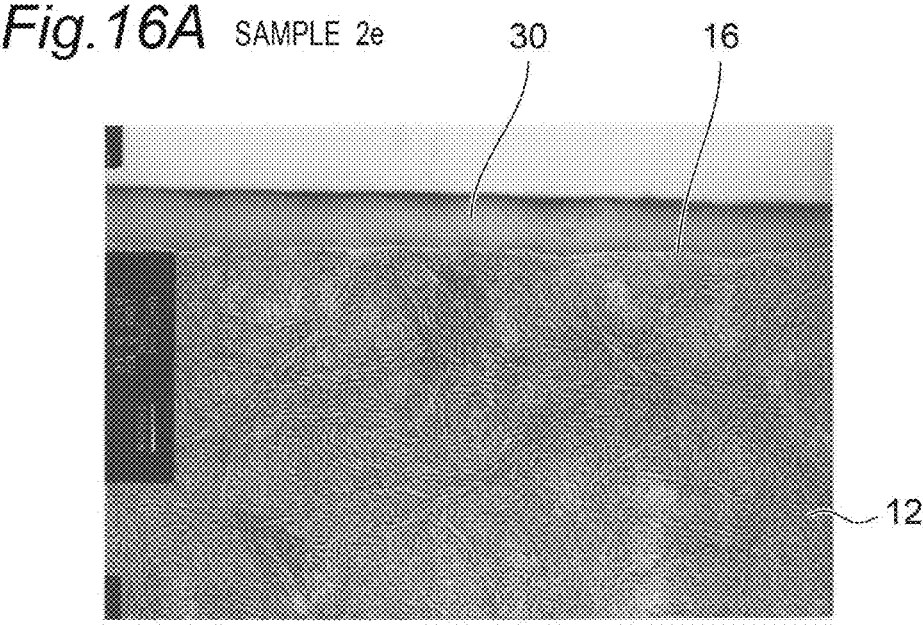
Fig.16A SAMPLE 2e
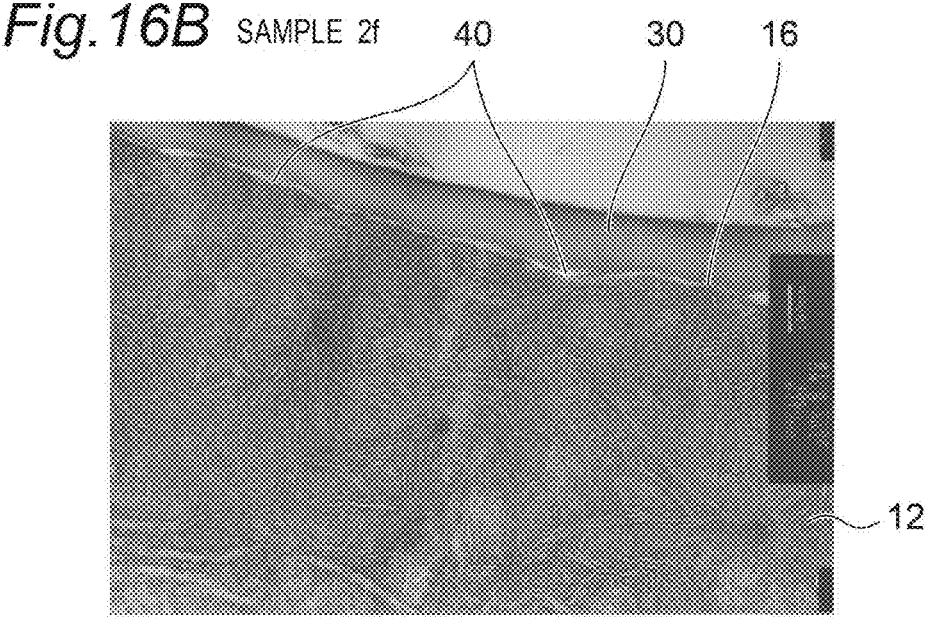
Fig.16B SAMPLE 2f

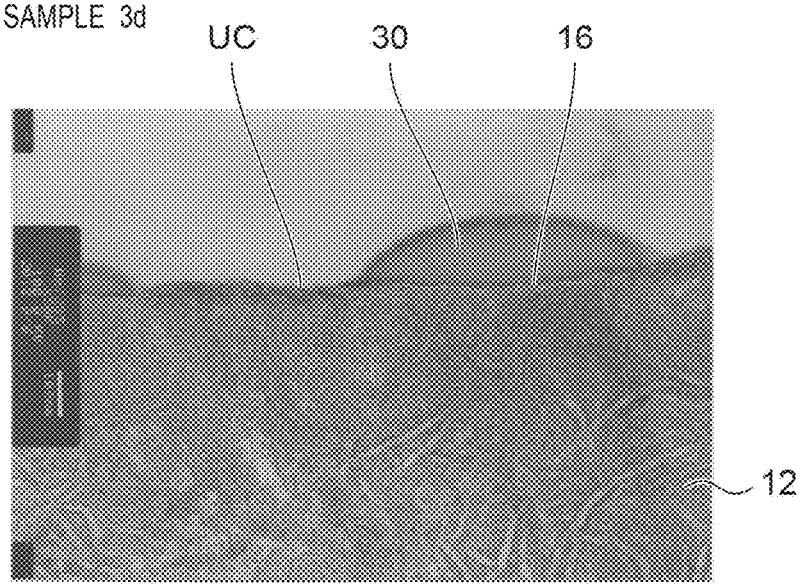
Fig.21A SAMPLE 3d
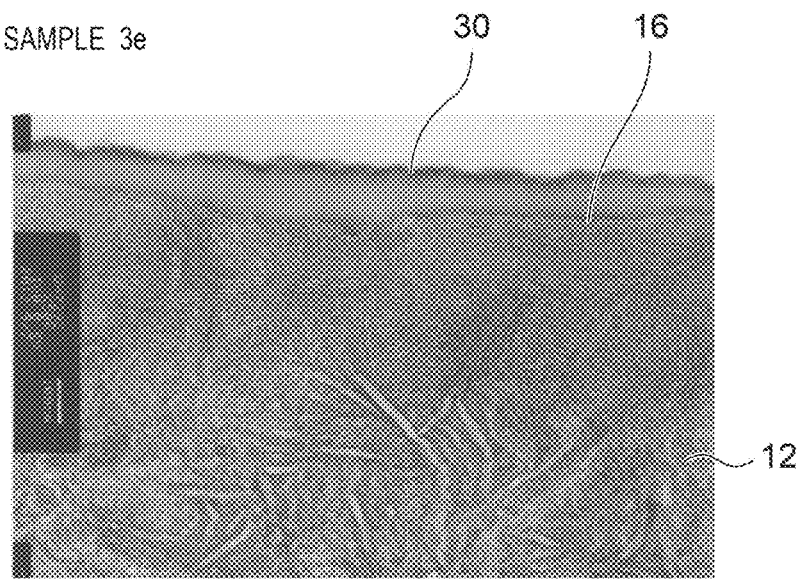
Fig.21B SAMPLE 3e

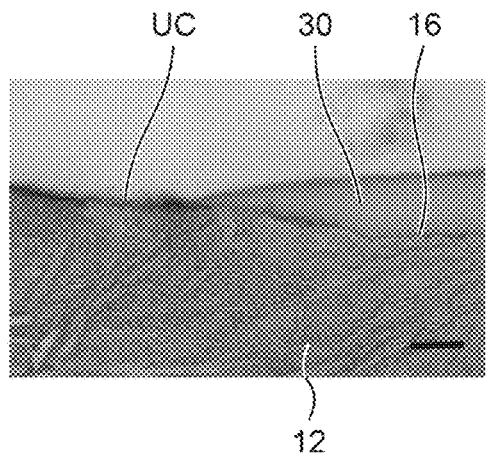
Fig.24A SAMPLE 4e
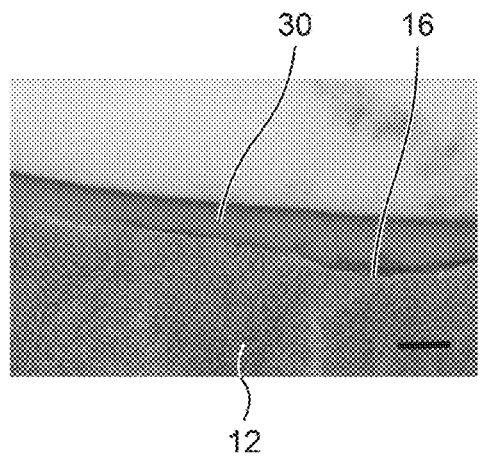
Fig.24B SAMPLE 4f
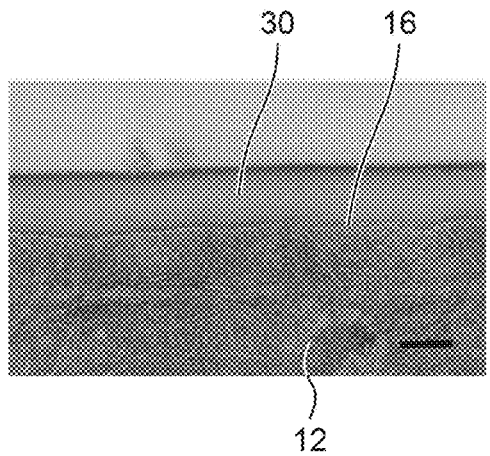
Fig.24C SAMPLE 4i
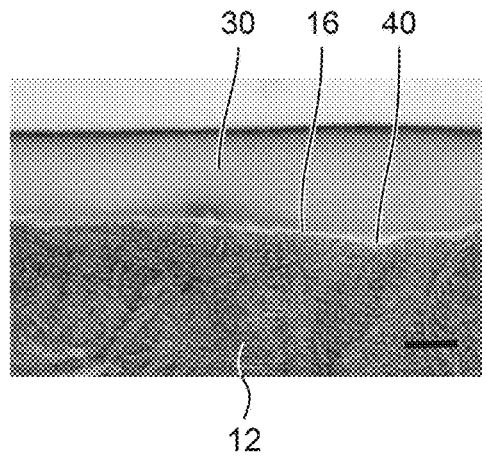
Fig.24D SAMPLE 4j

BEARING MATERIAL AND METHOD OF PRODUCING THE SAME

TECHNICAL FIELD

The present invention relates to a medical material and a method of producing the same, and particularly to a bearing material to be used for an artificial joint replacement, and a method of producing the same.

BACKGROUND ART

In recent days, with the progress of aging society, the number of patients in need of support and care has quickly increased. About 20 to 30% of these patients have disorders in functions of motors (skeletons such as joint and spinal, nerve for moving skeletons, muscle and ligament, etc.). In particular, loss of walking ability leads to an increase in the risk of other diseases such as dementia and visceral disease.

In the case of losing walking ability due to external injuries of a hip joint (bone fracture, etc.) or diseases of a hip joint (hip osteoarthritis, rheumatoid arthritis, etc.), one choice may be artificial hip joint replacement arthroplasty. The artificial hip joint replacement arthroplasty is an operation of replacing a hip joint with function disorder by an artificial joint replacement. The artificial hip joint replacement arthroplasty enables patients to not only recover walking ability, but also to get relief from pain of a hip joint.

Lifetime of various artificial joint replacements including an artificial hip joint replacement is usually said to be about 15 to 20 years. Therefore, patients may undergo a revision surgery of an artificial joint replacement (the revision surgery for the artificial joint replacement) 15 to 20 years after they underwent the artificial hip joint replacement arthroplasty. In order to avoid the revision artificial joint replacement arthroplasty as much as possible, an artificial joint replacement with longer lifetime is desired.

One reason for needing the revision surgery of the artificial joint replacement is loosening of an artificial joint replacement. For example, in a lot of artificial hip joint replacements, a liner made of polyethylene (PE), and a femoral head made of metal or ceramic are used. When the artificial joint replacement is operated, the liner made of a soft material is worn away by the femoral head made of a hard material to generate submicron-sized wear debris of PE. When macrophages eat the wear debris generated in the living body, macrophages accelerate formation of osteoclasts. As a result, osteolysis due to osteoclasts occurs in the bone surrounding the implant to form a gap between the bone and the artificial joint replacement, leading to loosening of the artificial joint replacement. In this way, loosening of the artificial joint replacement occurs due to the vital reaction against a foreign substance called "wear debris of PE".

Therefore, "reduction in generation of wear debris of PE (improvement in wear-resistance)" is effective so as to suppress loosening of the artificial joint replacement.

It has been known that a liner made of crosslinked PE (CLPE) is used so as to improve wear-resistance (for example, Patent Document 1). CLPE is obtained by irradiating common PE with high energy beams (a gamma-ray, an electron beam, etc.) to cause the crosslinking reaction. CLPE can reduce the generation of wear debris from the liner since it is excellent in wear-resistance as compared with the common PE.

However, when a free radical is generated in PE by irradiation with high energy beams, the molecular chain of PE may be cut by the free radical, leading to a decrease in mechanical strength of the liner. The liner disposed in the living body over a long period of time may cause a decrease in mechanical strength of the liner as a result of cutting of the molecular chain of PE due to oxidation. The decrease in mechanical strength of the liner is not desirable since it causes deterioration of load supportability and wear-resistance of the liner.

There has been made an attempt to produce a liner using PE including a radical scavenger (for example, vitamin A, vitamin C, and vitamin E) so as to inactivate a free radical in PE and to enhance oxidation resistance of PE (for example, Patent Document 2).

There has been known, as another attempt to improve wear-resistance, coating of a surface of the liner with a highly lubricating polymer film (for example, Patent Documents 3 to 5). There has been used, as the polymer film, a 2-methacryloyloxyethyl phosphorylcholine (MPC) film which exhibits extremely highly lubricity under wet environment.

Patent Document 1: JP 2000-514481 W
Patent Document 2: JP 4256096 B1
Patent Document 3: JP 2003-310649 A
Patent Document 4: JP 4963838 B1
Patent Document 5: JP 5028080 B1

DISCLOSURE OF THE INVENTION

Problems to be Solved by the Invention

There is a need to satisfy both wear-resistance and oxidation resistance of the liner so as to further prolong lifetime of an artificial joint replacement. If it is possible to produce a "liner including a substrate made of PE including a radical scavenger, and a highly lubricating polymer film covering a surface of the substrate" based on the contents disclosed, for example, in Patent Documents 2 and 3, it should be possible to obtain a liner capable of maintaining excellent wear-resistance and oxidation resistance over a long period of time by the synergistic effect of the radical scavenger and the polymer film.

However, the present inventors have produced such liner and, as a result, there arose a problem that a continuous polymer film is less likely to be formed or a polymer film is easily removed from a substrate, thus failing to achieve both wear-resistance and oxidation resistance to be expected.

An object of the present invention is to provide a method of producing a bearing material (liner) having excellent wear-resistance and oxidation resistance, and a bearing material obtained by the method of producing the same.

Means for Solving the Problems

The method of producing a bearing material according to the present invention includes the steps of molding a substrate including a radical scavenger and a polymer material; washing at least a part of a surface of the substrate with a washing liquid; and fixing a polymer chain having a phosphorylcholine group at at least the part of the surface by a graft bond after washing so as to form a polymer film on at least the part of the surface.

As a result of observation of a bearing material in which a polymer film is formed without the washing step, using an electron microscope, it has been confirmed that a continuous polymer film is less likely to be formed and a substrate surface is likely to be exposed from the defective portion (for example, hole of a polymer film, etc.) of the polymer film, or that a gap is formed at the interface between the formed polymer film and the substrate, and the polymer film is easily removed from the substrate. It is considered that the exposed substrate surface is likely to undergo wear as compared with a substrate surface covered with a polymer film, thus failing to obtain wear-resistance to be expected.

Meanwhile, like the present invention, it is possible to form a polymer film which is continuous (namely, polymer film with no defective portion) and is also excellent in adhesion with the substrate, after the washing step. Therefore, it is considered that a bearing material having excellent wear-resistance and oxidation resistance could be obtained.

In other words, according to the production method of the present invention, it is possible to obtain a bearing material having excellent wear-resistance by including the "step of washing at least a part of a surface of the substrate with a washing liquid".

The bearing material according to the present invention is produced by the above method.

Specifically, the bearing material according to the present invention is a bearing material including a substrate including a radical scavenger and a polymer material, and a polymer film covering at least a part of a surface of the substrate, wherein the polymer film includes a phosphorylcholine group-containing polymer chain graft-bonded to at least a part of the surface, and a contact angle of the polymer film with water is 40° or less.

The bearing material of the present invention is produced by the above method, and is excellent in adhesion with the substrate and also includes a continuous polymer film (namely, polymer film with no defective portion). Therefore, the bearing material of the present invention is excellent in wear-resistance.

In the continuous polymer film, the contact angle with water becomes 40° or less. Therefore, in the bearing material of the present invention, it is found that the polymer film covering the bearing material, includes a continuous polymer film since the contact angle with water is 40° or less. Therefore, the bearing material of the present invention is excellent in wear-resistance.

Effects of the Invention

According to the production method of the present invention, it is possible to produce a bearing material having excellent wear-resistance and oxidation resistance by including the step of washing with a washing liquid. The bearing material of the present invention is capable of obtaining an artificial joint replacement having long lifetime because of having excellent wear-resistance and oxidation resistance.

BRIEF DESCRIPTION OF THE DRAWINGS

FIG. 5A is a graph showing the measurement results of the surface atom concentration, and FIG. 5B is a graph showing the measurement results of the contact angle with water.

FIG. 9 is a graph showing the results of the wear test 2 of samples 1d, 1j, and 1k performed in Example 5.

FIGS. 15($a$) and 15($b$) are TEM images with respect to samples 2b and 2c taken in Example 12.

FIGS. 16($a$) and 16($b$) are TEM images with respect to samples 2e to 2f taken in Example 12.

FIGS. 21($a$) and 21($b$) are TEM images with respect to samples 3d and 3e taken in Example 18.

FIG. 23($a$) is a graph showing the measurement results of the contact angle with water, FIG. 23($b$) is a graph showing the measurement results of the phosphoric index, FIG. 23($c$) is a graph showing the measurement results of the film thickness, and FIG. 23($d$) is a graph showing the measurement results of the surface phosphorus atom concentration.

FIGS. 24($a$) to 24($d$) are TEM images with respect to samples 4e, 4f, 4i, and 4j taken in Example 26.

MODE FOR CARRYING OUT THE INVENTION

First Embodiment

Figure 1:
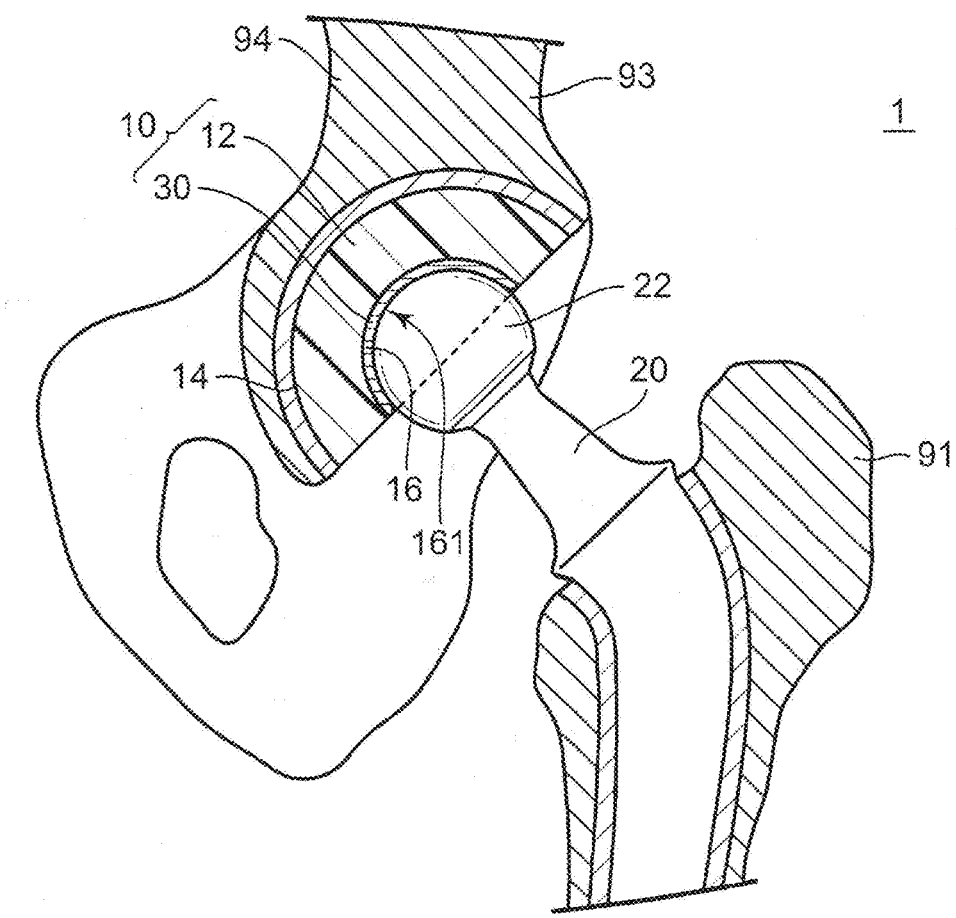
FIG. 1 is a schematic view of an artificial hip joint replacement using a bearing material according to First Embodiment.
Figure 2:
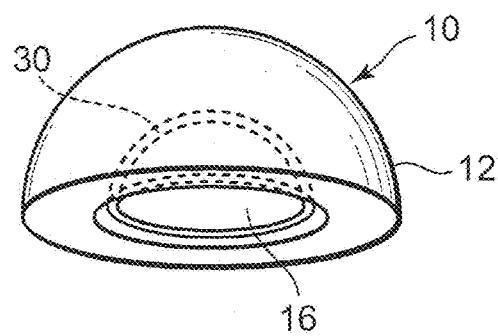
FIG. 2 is a schematic perspective view of the bearing material according to First Embodiment.

FIG. 1 is a schematic view of an artificial hip joint replacement 1. The artificial hip joint replacement 1 includes a bearing material (liner) 10 to be fixed to an acetabulum 94 of a hip bone 93, and a femoral stem 20 to be fixed to a proximal end of a femur 91. As shown in FIG. 1 and FIG. 2, a liner 10 includes a substrate 12 having an approximately hemispherical acetabulum fixing face 14 and an approximately hemispherically recessed bearing surface 16, and a polymer film 30 covering the bearing surface 16. A femoral head 22 of the femoral stem 20 is fitted in the bearing surface 16 covered with the polymer film 30 (a covered bearing surface 161), followed by sliding, thus functioning as a hip joint.

The substrate 12 of the liner 10 includes a radical scavenger and a polymer material. The substrate 12 may be made of the radical scavenger and the polymer material. It is possible to use, as the polymer material, for example, a PE-based material. The "radical scavenger" means a compound which scavenges radicals generated in the substrate 12 to inactivate them. The radical scavenger also has the capability of inactivating a substance which causes oxidation (reactive oxygen, etc.).

In the present invention, in order to form the substrate 12 of the liner 10, a material for substrate including a polymer material and a radical scavenger, is used. Therefore, even if free radicals are generated in the substrate 12 during the production process of the liner 10, free radicals are inactivated by the radical scavenger in the substrate material. Therefore, it is possible to suppress the polymer material composing the substrate 12 from causing deterioration due to free radicals. The substrate 12 including the radical scavenger can inactivate reactive oxygen and the like, which makes it possible to suppress the substrate 12 from causing oxidative deterioration in the living body due to the reactive oxygen and the like.

The polymer film 30 covering the surface of the bearing surface 16 is made of a polymer having a phosphorylcholine group. Specifically, the polymer film 30 has a structure in which polymer chains having a phosphorylcholine group are arranged on the surface. Such structure resembles a structure of a biofilm.

The biofilm composing a cartilage surface of a natural joint portion and the like is an assembly of phospholipid molecules. The surface of the biofilm is microscopically covered with phosphorylcholine groups (Ishihara: SURGERY, Vol. 61, pp. 132 (1999)). The natural articular cartilage composes a lubricant joint face having an extremely low friction coefficient by holding a lubricating liquid inside aggregates of the biofilm and a hydrophilic polymer including proteoglycan and hyaluronic acid. Like the natural articular cartilage, the polymer film 30 of the present invention can hold the lubricating liquid inside the polymer film 30 because of its high affinity with the lubricating liquid. Therefore, as compared with a conventional liner 10 in which the bearing surface 16 is not covered with the polymer film 30, the friction coefficient of the liner 10 of the present invention, in which the bearing surface 16 is covered with the polymer film 30, decreases.

Coating of the bearing surface 16 of the substrate 12 made of PE with the polymer film 30 enables the contact angle with water on the bearing surface 16 (hereinafter referred to as a "contact angle") to decrease from about 90° (contact angle on PE which is not covered with the polymer film 30) to about 14° (contact angle on an ideal polymer film 30).

Deterioration of continuity of the polymer film 30 leads to an increase in contact angle. Therefore, the value of the contact angle can serve as an indicator for knowing the continuity of the polymer film 30. Meanwhile, the continuous polymer film 30 exerts high effect of improving tribological characteristic (for example, wear-resistance) of the liner 10, as compared with the discontinuous polymer film 30 (for example, a polymer film 30 with the defective portion such as hole, polymer film 30 distributed in an island shape, etc.). Therefore, the value of the contact angle can also serve as an indicator for knowing tribological characteristic of the liner 10.

When the polymer film 30 covering the bearing surface 16 of the liner 10 has a contact angle of 40° or less, it is possible to significantly improve the wear-resistance of the liner 10. This reason is considered that partial wear can be suppressed since holes having the size to cause deterioration of the wear-resistance do not exist in the polymer film 30 having a contact angle of 40° or less.

In this way, coating of the bearing surface 16 with the polymer film 30 having a contact angle of 40° or less enables partial wear to be less likely to be formed on the bearing surface 16 of the substrate 12, which makes it possible to obtain a liner 10 having excellent wear-resistance. Therefore, use of such liner 10 enables prolongation of lifetime of an artificial joint replacement. In particular, coating of the bearing surface 16 with the polymer film 30 having a contact angle of 35° or less is more preferable since the continuity of the polymer film 30 is more enhanced, leading to further prolongation of lifetime. Furthermore, coating of the bearing surface 16 with the polymer film 30 having a contact angle of 15° or less is still more preferable since the continuity of the polymer film 30 is still more enhanced, leading to significant prolongation of lifetime.

The more the defective portion of the polymer film 30 becomes fewer, the density of the polymer film 30 increases. Therefore, the more the density of the polymer film 30 of the liner 10 becomes higher, the wear-resistance of the liner 10 increases. It is possible to use, as the indicator for knowing the density of the polymer chain, the atom concentration of phosphorus and nitrogen atoms.

A single molecule of a monomer having a phosphorylcholine group has each one of phosphorus and nitrogen atoms. Therefore, the content of phosphorus and nitrogen atoms in the measuring range (corresponding to the atom concentration) is proportional to the number of monomers existing within the range. In other words, the atom concentration of phosphorus and nitrogen atoms can serve as an indicator for knowing the density of the polymer film 30.

X-ray photoelectron spectroscopy (XPS) analysis can be used to determine the atom concentration of phosphorus and nitrogen atoms. XPS has a merit of being capable of measuring even if a surface of a sample has an irregular shape because of very small analysis region.

Regarding theoretic atom concentration of a defect-free 2-methacryloyloxyethyl phosphorylcholine (MPC) polymer film, phosphorus atom concentration is 5.3 atom % and nitrogen atom concentration is 5.3 atom %. Therefore, it can be estimated that the polymer film 30 with fewer defects is formed as each atom concentration becomes closer to the theoretic value. In other words, it is considered that as each atom concentration becomes closer to the theoretic value, the obtained liner 10 exhibits higher affinity to the lubricating liquid of the polymer film 30 and is excellent in characteristics such as wear-resistance.

In the polymer film 30, the phosphorus atom concentration obtained from XPS analysis is preferably 3.5 atom % or more, and the nitrogen atom concentration is preferably 3.5 atom % or more. The polymer film 30 having such atom concentration is considered to be a polymer film 30 having high density. The bearing surface 16 covered with such polymer film 30 is less likely to undergo wear, which makes it possible to form an artificial joint replacement having satisfactory wear-resistance.

The phosphorus atom concentration of the polymer film 30 is more preferably 4.5 atom % to 5.3 atom %, and still more preferably 5.0 atom % to 5.3 atom %. The nitrogen atom concentration of the polymer film 30 is more preferably 4.5 atom % to 5.3 atom %, and still more preferably 5.0 atom % to 5.3 atom %. The polymer film 30 having such high atom concentration is considered to be a polymer film 30 having higher density and fewer holes. Therefore, an artificial joint replacement having excellent wear-resistance can be formed.

The phosphorus atom concentration and the nitrogen atom concentration are excellent as an indicator for knowing the density of the polymer film 30, but do not sometimes reflect the presence or absence of holes when the polymer film 30 is macroscopically observed for the following reason. That is, because of very small XPS analysis region, there is some possibility of taking place a situation that no hole exists in the measuring range even if holes exist in the polymer film 30 when macroscopically observed. In the case of evaluating the polymer film 30, it is desirable to comprehensively judge based on the results of the atom concentration and the results of the macroscopic measurement of physical properties (for example, contact angle with water) of the polymer film 30, not to judge only by the results of the atom concentration.

When the polymer chain composing the polymer film 30 becomes longer (namely, when the film thickness of the polymer film 30 increases), the continuity of the polymer film 30 is improved for the following reason. That is, when the polymer film 30 has a small thickness, the portion recognized as the "defective portion (for example, holes)" of the polymer film 30 is covered by lengthening the polymer chain around the defective portion. However, the polymer chain covering the portion recognized as the defective portion is not bonded to the bearing surface 16 of the substrate 12 exposed from the defective portion of the polymer film 30. Therefore, on cross-sectional viewing of the polymer film 30, a gap is formed between the bearing surface 16 and the polymer film 30 of the substrate 12.

When the gap exists between the bearing surface 16 and the polymer film 30 of the substrate 12, a force of the polymer film 30 bonded to the bearing surface 16 decreases. Therefore, the delamination strength of the polymer film 30 may decrease. In other words, when no gap substantially exists between the bearing surface 16 and the polymer film 30 of the substrate 12, a force of the polymer film 30 bonded to the bearing surface 16 is high. Therefore, when using, as the artificial joint replacement, the liner 10 with the polymer film 30 in which no gap substantially exist, the possibility of removing of the polymer film 30 from the substrate 12 decreases, which makes it possible to prolong lifetime of the artificial joint replacement.

Figure 3:
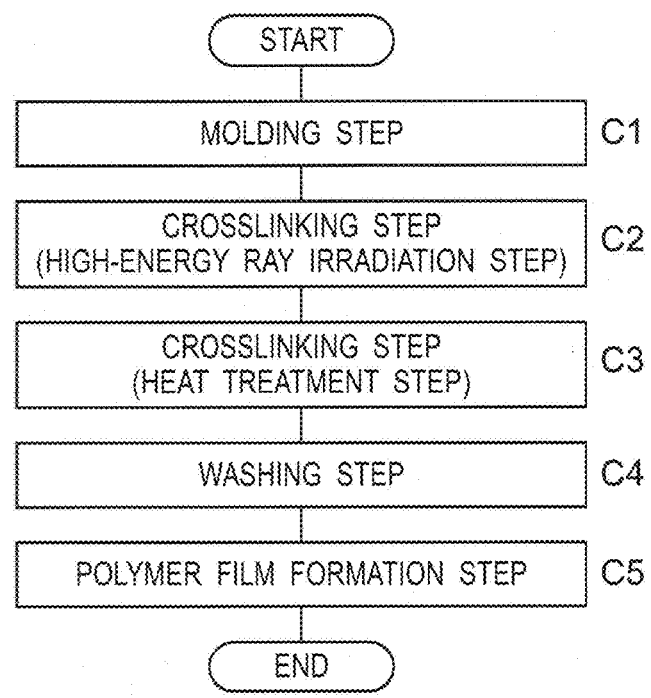
FIG. 3 is a flow chart of a method of producing the bearing material according to First Embodiment.

The method of producing a bearing material according to the present invention (liner 10) will be described with reference to FIG. 3.

The method of producing a liner 10 includes:

1. Step of molding a substrate 12 (molding step C1);
2. Step of washing a part (bearing surface 16) of the substrate surface (washing step C4); and
3. Step of forming a polymer film 30 on the bearing surface 16 (polymer film forming step C5).

The method may include the crosslinking steps C2 and C3 of crosslinking a polymer material included in the substrate 12 between the molding step C1 and the washing step C4.

Each step will be described in detail below.

(1. Step of Molding Substrate 12: Molding Step C1)

In this step, a substrate 12 including a radical scavenger and a polymer material is molded. It is possible to employ, as molding means, a processing method in which a block of a substrate material including a radical scavenger and a polymer material, is prepared and the block-shaped substrate material is molded into a shape of a substrate 12 by cutting. The block-shaped substrate material can be produced, for example, by mixing a powdered, granular, or pelletized polymer material (for example, ultrahigh molecular weight PE (UHMWPE) material) with a radical scavenger (liquid or powdered), followed by compression molding, extrusion molding, or injection molding of the obtained mixture. When using UHMWPE as the polymer material, UHMWPE is a thermoplastic resin and exhibits low fluidity even at a melting temperature or higher and, therefore, a solid (particularly, powdered or granular) UHMWPE may be molded under high-temperature and high-pressure conditions after placing in a mold.

Here, compression molding can include, for example, a normal-temperature compression stage, a pressure dropping and temperature rising stage, a high-temperature and high-pressure maintaining stage, and a cooling stage.

In the normal-temperature compression stage, a raw powder of a mixture of UHMWPE and a radical scavenger is placed in a mold and then compressed (pressed) under a pressure of 200 to 250 MPa at a temperature of 25° C. (normal temperature) for 1 to 10 minutes.

In the pressure dropping and temperature rising stage, the pressure is dropped to a range of 20 to 35 MPa from the value set in the normal-temperature compression stage, and the temperature is raised from 25° C. to a range of 140 to 275° C., followed by maintaining for 10 to 40 minutes.

In the high-temperature and high-pressure maintaining stage, the pressure is increased to a range of 100 to 180 MPa from the value set in the pressure dropping and temperature rising stage in a state where the temperature is maintained at high temperature set in the pressure dropping and temperature rising stage, followed by maintaining for 1 to 10 minutes.

In the cooling stage, the temperature is gradually cooled to 25° C. (normal temperature) from the value set in the high-temperature and high-pressure maintaining stage over 10 to 50 minutes in a state where the pressure is maintained at the value set in the high-temperature and high-pressure maintaining stage.

Finally, after releasing the pressure, the product is removed from the mold to obtain a compression molded article. The radical scavenger such as vitamin E is contained in the compression molded article obtained.

The substrate material obtained by compression molding, extrusion molding, or injection molding can be subjected to a polymer film forming step after adjusting the shape by cutting.

It is also possible to use a molding method in which a mixed powder is molded into a shape of the substrate 12 by compression molding or injection molding (so-called near net shape molding method). The substrate 12 molded by the near net shape molding method does not need cutting or may be slightly cut, which makes it possible to reduce cost and labor required for cutting.

(Crosslinking Step (High Energy Beam Irradiation Step) C2)

In order to enhance the wear-resistance of the substrate 12, the polymer material composing the substrate 12 may be subjected to a crosslinking treatment. For example, a block-shaped substrate material before molding is irradiated with high energy beams (for example, the X-ray, the gamma-ray, or the electron beam) to crosslink a polymer material (for example, PE) included in the substrate material to produce a "crosslinked block-shaped substrate material (crosslinked polymer material (for example, CLPE), and then the obtained "crosslinked block-shaped substrate material" is cut, and a substrate 12 is obtained.

In the crosslinking treatment, the material for substrate is irradiated with high energy beams to generate free radicals in the polymer material included in the substrate material. Free radicals enable formation of bonding between molecular chains of the polymer material, leading to the polymer material having a network structure (crosslink, CL). The network structure causes an increase in bonding force between molecular chains of the polymer material and therefore improves mechanical properties (for example, wear-resistance, impact resistance, etc.) of the polymer material.

In another example, first, a substrate 12 including a polymer material (for example, PE) is prepared, and then the polymer material may be subjected to a crosslinking treatment by irradiating the substrate 12 with high energy beams.

Like the present invention, in the case of the substrate 12 including a radical scavenger, radicals generated in the substrate 12 are partially scavenged by the radical scavenger and therefore the crosslinking reaction is less likely to proceed. Therefore, there is a need to irradiate with high energy beams at comparatively high dose (for example, 75 kGy to 200 kGy, and more preferably 100 kGy to 150 kGy) so as to allow the crosslinking reaction to sufficiently proceed in the substrate 12 including a radical scavenger. In the case of PE including no radical scavenger, irradiation with high energy beams at a dose of 50 to 100 kGy allows the crosslinking reaction to sufficiently proceed.

(Crosslinking Step (Heat Treatment Step) C3)

After irradiation with high energy beams, the polymer material may be subjected to a heat treatment. Since free radicals generated in the polymer material by irradiation with high energy beams as a result of the heat treatment efficiently because the crosslinking reaction, the crosslinking reaction is accelerated. The temperature of the heat treatment is preferably from 110 to 130° C., and the treatment time of the heat treatment is preferably from 2 to 12 hours.

In this way, the crosslinking treatment can also be performed even before or after molding. However, the crosslinking treatment is preferably performed before molding for the following reason. Since irradiation with high energy beams needed for the crosslinking treatment may cause a change in size of the substrate 12, it is not preferred to perform the crosslinking treatment after molding. The crosslinking treatment is desirably performed before "2. Step of washing a bearing surface 16" for the following reason.

In the present invention, "3. Step of forming a polymer film" is performed after "2. Step of washing a bearing surface 16". Since the washing effect of the bearing surface 16 deteriorates with time, it is not desired to perform another treatment (for example, crosslinking treatment) during these steps. Since irradiation with high energy beams needed for the crosslinking treatment is not preferred for the polymer film 30, it is not desired to perform the crosslinking treatment after "3. Step of forming a polymer film". For these reasons, it is preferred to perform the crosslinking treatment before the washing step.

It is also possible to perform the crosslinking treatment of the polymer material by adding a crosslinking agent to a substrate material. However, since the liner 10 to be used in the artificial joint replacement is disposed in the living body over a long period of time, it is not preferred to use a crosslinking agent having uncertain safety.

(2. Step of Washing Bearing Surface 16: Washing Step C4)

In this step, at least a part (specifically, bearing surface 16) of the substrate 12 is washed with a washing liquid. This step enables formation of a polymer film 30 with fewer defects on a bearing surface 16 in the subsequent "3. Step of forming a polymer film 30".

In order to form the polymer film 30, a polymer chain composing the polymer film 30 is graft-bonded to the bearing surface 16 of the substrate 12. Graft bonding makes it possible to stably fix the polymer chain on the bearing surface 16 of the substrate 12. It is also possible to increase a polymerization starting point by controlling the conditions upon graft bonding (for example, increase in ultraviolet-ray irradiation intensity, increase in polymerization initiator concentration, prolongation of ultraviolet-ray irradiation time, etc.). As a result, a lot of phosphorylcholine chains can be formed on the bearing surface of the substrate, and therefore a density of the polymer film can be increased.

Meanwhile, when the radical scavenger exists on the bearing surface 16 of the substrate 12, there is a tendency that the polymer chain is less likely to be graft-bonded to the bearing surface 16. This reason is considered as follows: the radical scavenger exists between a monomer forming the polymer film 30 and the bearing surface 16, and the monomer cannot approach the bearing surface 16, and therefore the polymer chain cannot be graft-bonded in the near-field region. Therefore, in the near-field region of the bearing surface 16, a hole is formed in the polymer film 30 and/or a gap is formed between the polymer film 30 and the bearing surface 16.

The polymer chain composing the polymer film 30 is formed by the surface starting graft polymerization reaction using radicals generated on a surface of the bearing surface 16. However, the radical scavenger contained in the polymer material scavenges radicals needed for the radical polymerization to inactivate them, which makes it possible to suppress the surface starting graft polymerization reaction. This is also considered to be one of causes for the generation of holes and gaps of the polymer film 30.

When the bearing surface 16 is washed before formation of the polymer film 30 to remove the radical scavenger only from the bearing surface 16, it becomes possible that a monomer forming the polymer film 30 approaches over the entire bearing surface 16. As a result, it becomes possible to form a polymer film 30, which is free from defects such as holes and gaps, or has fewer defects.

As mentioned above, an object of the washing step is to wash the radical scavenger of the bearing surface 16. Therefore, the washing liquid to be used is suitably those which exert high effect of washing the radical scavenger. Meanwhile, it is not preferred to use, as the washing liquid, an organic solvent capable of dissolving the polymer material composing the substrate 12 since it may cause damage to a surface of the bearing surface 16. Use of the organic solvent is not also preferred since it may cause a decrease in concentration of the radical scavenger contained inside the polymer material, leading to deterioration of antioxidant ability of the liner 10. Therefore, it is preferred to use, as the washing liquid, an aqueous solution containing a surfactant. A lipophilic radical scavenger can be removed by the washing effect of the surfactant, and a hydrophilic radical scavenger can be removed by water as a solvent. The aqueous solution containing a surfactant also has a merit of having very low possibility of causing damage to the substrate 12 made of an organic material.

In the washing step, washing can be performed under the conditions of the washing temperature of 40 to 80° C., and more preferably 70 to 80° C., and the washing time of 6 to 48 hours, and more preferably 12 to 48 hours, in a state where a substrate is immersed in a washing liquid containing a surfactant. When washing is performed under these conditions, it is possible to form a polymer film 30 with significantly fewer defects such as holes and gaps when the polymer film 30 is formed in the subsequent step. When washing is performed, for example, under the conditions of the washing temperature of 70° C. and the washing time of 6 hours, a polymer film 30 with fewer defects can be formed. When the washing temperature is lower than 70° C., the same effect can be obtained by increasing the washing time to more than 6 hours. When the washing temperature is higher than 70° C., the same effect can be obtained even if the washing time is decreased to less than 6 hours.

(3. Step of Forming Polymer Film 30: Polymer Film Forming Step C5)

In this step, a polymer chain having a phosphorylcholine group is grafted from at least a part (specifically, bearing surface 16) of a substrate 12 after washing so as to form a polymer film 30 on a bearing surface 16. Since the polymer film 30 is formed so as to reduce a friction coefficient of the bearing surface 16 of the substrate 12, the polymer film may be formed at least on the bearing surface 16 of the substrate 12. For example, in the case of producing an acetabular cup in an artificial hip joint replacement, at least a polymer film may be formed on a cup inner sphere face on which a femoral head ball slides.

In order to producing the liner 10 according to the present invention, the polymer film 30 has to be fixed on the bearing surface 16 of the liner 10. Some fixing methods have hitherto been known. In the present invention, the polymer film 30 is fixed by grafting a polymerizable monomer as a compound having a phosphorylcholine group (PC compound) from the bearing surface 16 by the graft polymerization reaction which is started on the bearing surface 16. This method has a merit that only the bearing surface 16 can be modified without causing deterioration of performances such as strength of a polymer material composing the liner 10, and also the bonding portion is chemically stabilized, and a large amount of phosphorylcholine groups are formed on the bearing surface of an artificial joint component, thus enabling an increase in density of the polymer film 30.

Specific procedure of forming a polymer film 30 includes irradiation with an ultraviolet-ray in a state where a polymerizable monomer having a phosphorylcholine group is in contact with a bearing surface 16. The ultraviolet-ray intensity is preferably 0.5 mW/cm² or more, and therefore a polymer film 30 can be formed on the bearing surface 16.

The irradiation intensity is more preferably 1.0 mW/cm² to 13.0 mW/cm², and therefore a polymer film 30 with fewer defects can be formed.

The irradiation intensity is more preferably 1.0 mW/cm² to 9.5 mW/cm², and particularly preferably 2.0 mW/cm² to 9.5 mW/cm², and therefore a polymer film 30 with still fewer defects can be formed.

From the viewpoint of production efficiency, the irradiation intensity is most preferably 2.0 mW/cm² to 5.0 mW/cm². When the irradiation intensity is within the above range, a polymer film 30 with significantly fewer defects can be formed.

The irradiation time of the ultraviolet-ray is preferably 0.5 hours to 24 hours. For example, when the ultraviolet-ray irradiation intensity is 0.5 mW/cm² or more, a continuous polymer film 30 can be formed on a bearing surface 16.

The irradiation time is more preferably 0.5 hours to 12 hours. For example, when the ultraviolet-ray irradiation intensity is 1.0 mW/cm² or more, a continuous polymer film 30 can be formed on a bearing surface 16.

The irradiation time is more preferably 0.5 hours to 6 hours. For example, when the ultraviolet-ray irradiation intensity is 2.0 mW/cm² or more, a continuous polymer film 30 can be formed on a bearing surface 16.

The irradiation time is particularly preferably 0.5 hours to 3 hours. For example, when the ultraviolet-ray irradiation intensity is 5.0 mW/cm² or more, a continuous polymer film 30 can be formed on a bearing surface 16. From the viewpoint of production efficiency, the irradiation time is preferably 3 hours or less.

When the ultraviolet-ray to be irradiated in the case of forming a polymer film 30 is expressed in terms of total energy (=intensity (mW/cm²)×time (seconds)), the total energy is preferably 6,000 mJ/cm² to 70,000 mJ/cm², and a continuous polymer film 30 can be formed on a bearing surface 16.

The total energy is more preferably 7,000 mJ/cm² to 50,000 mJ/cm², and therefore a polymer film 30 with fewer defects can be formed.

The total energy is more preferably 10,000 mJ/cm² to 45,000 mJ/cm², and therefore a polymer film 30 with still fewer defects can be formed.

In order to bring a polymerizable monomer having a phosphorylcholine group into contact with a bearing surface 16, for example, the bearing surface 16 of a liner 10 may be immersed in an aqueous solution containing a polymerizable monomer. A polymer film 30 can be formed on the bearing surface 16 by irradiating the bearing surface 16 with the ultraviolet-ray in a state of being immersed in the aqueous solution.

The concentration of the polymerizable monomer in the aqueous solution is preferably 0.15 mol/L to 1.0 mol/L, and therefore a polymer film 30 on a bearing surface 16 can be formed.

The concentration of the polymerizable monomer is more preferably 0.27 mol/L to 1.0 mol/L, and therefore a continuous polymer film 30 can be formed.

The concentration of the polymerizable monomer is more preferably 0.27 mol/L to 0.8 mol/L, particularly preferably 0.27 mol/L to 0.55 mol/L, and therefore a polymer film 30 with fewer defects can be formed.

From the viewpoint of formation of a preferable polymer film 30, the concentration of the polymerizable monomer may exceed 1.0 mol/L. However, when an aqueous solution having a concentration of more than 1.0 mol/L is prepared, it becomes very difficult to dissolve a polymerizable monomer in a water solvent. Since the polymerizable monomer is expensive, when using an aqueous solution having a concentration of more than 1.0 mol/L, production cost of a bearing material may increase.

Before irradiation with the ultraviolet-ray, a photoinduced polymerization initiator may be applied on at least a part (specifically, bearing surface 16) of a substrate 12. The photoinduced polymerization initiator is a compound which is excited by irradiating with light having a wavelength needed for excitation (for example, the ultraviolet-ray, etc.) at the intensity needed for excitation to generate radicals. When the photoinduced polymerization initiator applied on a bearing surface 16 is irradiated with the ultraviolet-ray, first, radicals are generated in the photoinduced polymerization initiator. Subsequently, radicals generated move to the bearing surface 16 and the moved radicals on a surface of the bearing surface 16 react with a polymerizable monomer in an aqueous solution to start graft copolymerization. The polymerizable monomer in the aqueous solution is successively polymerized to form a polymer chain. A polymer film 30 includes an assembly of polymer chains covering the bearing surface 16.

Taking the growth process of such polymer chain into consideration, it is estimated that the thickness of the polymer film 30 is influenced by the concentration of the polymerizable monomer in the aqueous solution.

In the growth process of the polymer chain, when the polymerizable monomer in the aqueous solution comes into contact with radicals at the end of the polymer chain, the polymerizable monomer is attacked by radicals, and therefore the polymerization proceeds. In order to grow the polymer chain longer, there is a need to enhance the contact probability so that the polymerizable monomer comes into contact with radicals before the termination reaction of radicals occurs.

It is considered that the polymerizable monomer concentration of the aqueous solution and the temperature of the aqueous solution exert an influence on the contact probability between the polymerizable monomer and radicals. For example, too low polymerizable monomer concentration will lead to low probability of meeting of radicals with the polymerizable monomer, thus increasing radicals which are inactivated before contacting with the polymerizable monomer. Too low temperature of the aqueous solution will lead to a decrease in motility of the monomer in the aqueous solution and low probability of meeting of radicals with the polymerizable monomer, thus increasing radicals which are inactivated before contacting with the polymerizable monomer. As a result, a short polymer chain (namely, thin polymer film 30) will be formed. Therefore, a long polymer chain (namely, thin polymer film 30) will be formed. In order to lengthen the polymer chain (namely, in order to thicken the polymer film 30), it is considered that an aqueous polymerizable monomer solution having a given concentration or more and a given temperature or more should be used.

Appropriate concentration of the aqueous polymerizable monomer solution can vary depending on other polymerization conditions and may be, for example, 0.15 mol/L or more. Appropriate temperature of the aqueous polymerizable monomer solution can vary depending on other polymerization conditions and may be, for example, 40° C. or higher.

The density of the obtained polymer film 30 can vary depending on the intensity and irradiation time of the ultraviolet-ray.

After the polymer film forming step, a sterilization treatment due to irradiation with the gamma-ray is preferably performed.

The material suited for the bearing material and the method of producing the same of the present invention will be described in detail below.

(Substrate 12)

A substrate 12 of a liner 10 is molded from a substrate material including a polymer material and a radical scavenger.

(Polymer Material)

It is preferred to use, as the polymer material contained in the substrate 12, for example, a PE-based material, and an ultrahigh molecular weight polyethylene (UHMWPE) is particularly preferably used. UHMWPE is suited for the substrate 12 since it is excellent in mechanical properties such as wear-resistance and deformation resistance among PE-based materials. Since the wear-resistance of UHMWPE is enhanced as the molecular weight increases, it is preferred to use UHMWPE having a molecular weight of at least $1\times10^6$ g/mol (1,000,000 g/mol) or more, preferably a molecular weight of $3\times10^6$ g/mol (3,000,000 g/mol) or more, more preferably $3\times10^6$ g/mol (3,000,000 g/mol) to $7\times10^6$ g/mol (7,000,000 g/mol), and particularly preferably $3\times10^6$ g/mol (3,000,000 g/mol) to $4\times10^6$ g/mol (4,000,000 g/mol).

Here, the molecular weight of UHMWPE composing the substrate is determined by measuring the viscosity of a decahydronaphthalene (decalin) solution at 135° C. according to the following equation (1).

[Equation 1]

$$\text{Molecular weight} = 5.37 \times 10^4 \times (\text{intrinsic viscosity})^{1.49} \quad (1)$$

(Radical Scavenger)

The radical scavenger contained in the substrate 12 is preferably a radical scavenger having a phenolic hydroxyl group or a tocotrienol group. In particular, a radical scavenger having a tocotrienol group is more preferably because of its higher antioxidant ability than that of a radical scavenger having tocopherol group.

It is possible to use, as specific examples of the radical scavenger, a hindered amine-based radical scavenger, a hindered phenol-based radical scavenger, a phosphorous-based radical scavenger, a sulfur-based radical scavenger, and the like.

Examples of the hindered amine-based radical scavenger include 1,2,2,6,6,-pentamethylpiperidinyl methacrylate, 2,2,6,6,-tetramethylpiperidinyl methacrylate, bis(2,2,6,6-tetramethyl-4-piperidine)sebacate, a polymer of dimethyl succinate and 4-hydroxy-2,2,6,6-tetramethyl-1-piperidine ethanol, N,N',N'',N'''-tetrakis-(4,6-bis-(butyl-(N-methyl-2,2,6,6-tetramethylpiperidin-4-yl)amino)-triazin-2-yl)-4,7-diazadecane-1,10-diamine, bis(2,2,6,6-tetramethyl-1-(octyloxy)-4-piperidinyl)decanedioate, bis(1,2,2,6,6-pentamethyl-4-piperidyl) [[3,5-bis(1,1-dimethylethyl)-4-hydroxyphenyl]methyl]butyl malonate, a reaction product of (a reaction product of cyclohexane with peroxidized N-butyl-2,2,6,6-tetramethyl-4-piperidine amine-2,4,6-trichloro-1,3,5-triazine) with 2-aminoethanol, bis(1,2,2,6,6-pentamethyl-4-piperidyl)sebacate, methyl-1,2,2,6,6-pentamethyl-4-piperidyl sebacate, tetrakis(1,2,2,6,6-pentamethyl-4-piperidine)-1,2,3,4-butanetetracarboxylate, and the like.

Examples of the hindered phenol-based radical scavenger include 2-t-butyl-4-methoxyphenol, 3-t-butyl-4-methoxyphenol, 2,6-di-t-butyl-4-ethylphenol, 2,2'-methylene-bis(4-methyl-6-t-butylphenol), 4,4'-thiobis-(3-methyl-6-t-butylphenol), 4,4'-butylidenebis(3-methyl-6-t-butylphenol), 1,1,3-tris(2-methyl-4-hydroxy-5-t-butylphenyl)butane, 1,3,5-trimethyl-2,4,6-tris(3,5-di-t-butyl-4-hydroxybenzyl) benzene, tetrakis-[methylene-3-(3',5'-di-t-butyl-4'-hydroxyphenyl)propionate]methane, and the like.

Examples of the phosphorous-based radical scavenger include triphenyl phosphite, diphenylisodecyl phosphite, phenyldiisodecyl phosphite, 4,4'-butylidene-bis(3-methyl-6-t-butylphenylditridecyl)phosphite, cyclic neopentanetetraylbis(nonylphenyl)phosphite, cyclic neopentanetetraylbis(dinonylphenyl)phosphite, cyclic neopentanetetrayltris(nonylphenyl)phosphite, cyclic neopentanetetrayltris(dinonylphenyl)phosphite, 10-(2,5-dihydroxyphenyl)-10H-9-oxa-10-phosphaphenanthrene-10-oxide, diisodecylpentaerythritol diphosphite, tris(2,4-di-t-butylphenyl)phosphate, and the like.

Examples of the sulfur-based radical scavenger include dilauryl 3,3'-thiodipropionate, distearyl 3,3'-thiodipropionate, N-cyclohexylthiophthalimide, N-n-butylbenzenesulfonamide, and the like.

It is also possible to use, as the radical scavenger, fat-soluble vitamin E (tocopherols).

The fat-soluble vitamin E includes tocopherol and tocotrienol, derivatives thereof, and the like, and examples thereof include tocopherols and derivatives thereof, such as α-tocopherol, β-tocopherol, γ-tocopherol, δ-tocopherol, dl-α-tocopherol, dl-β-tocopherol, dl-γ-tocopherol, dl-δ-tocopherol, dl-α-tocopherol acetate, dl-α-tocopherol nicotinate, dl-α-tocopherol linoleate, and dl-α-tocopherol succinate, α-tocotrienol, β-tocotrienol, γ-tocotrienol, δ-tocotrienol, and the like. These radical scavengers may be used alone, or plural radical scavengers may be used in combination. It is preferred to use in a state of a mixture, and the radical scavenge in a state of a mixture includes those called extracted tocopherol, mix tocopherol, and the like.

Among these radical scavengers, vitamin E and a hindered amine-based compound are preferable. The vitamin E and hindered amine-based compound are suited for use in the substrate 12 to be used in the living body since biosafety thereof is confirmed.

It is also possible to use, as the radical scavenger, vitamins such as vitamin A and vitamin C, aromatic amines, amines having an aldehyde group or a ketone group, and salts and condensates of aminophenol, in addition to the above-mentioned radical scavengers.

From the viewpoint of the oxidation prevention effect, the content of the radical scavenger is preferably 0.01 to 5% by weight, more preferably 0.05 to 0.7% by weight, and particularly preferably 0.05 to 0.15% by weight, based on the polymer material composing the substrate 12.

(Polymer Film 30)

A polymerizable monomer having a phosphorylcholine group is used to form a polymer film 30. In particular, selection of a monomer having a phosphorylcholine group at one end and a functional group capable of graft-copolymerizing with a polymer material composing the liner 10 at the other end enables graft bonding of the polymer film 30 to the bearing surface 16 of the liner 10.

Examples of the polymerizable monomer suited for the present invention include 2-methacryloyloxyethyl phosphorylcholine, 2-acryloyloxyethyl phosphorylcholine, 4-methacryloyloxybutyl phosphorylcholine, 6-methacryloyloxyhexyl phosphorylcholine, ω-methacryloyloxyethylene phosphorylcholine, 4-styryloxybutyl phosphorylcholine, and the like. In particular, 2-methacryloyloxyethyl phosphorylcholine (MPC) is preferable.

The MPC monomer has a chemical structural formula shown below, and includes a phosphorylcholine group and a polymerizable methacrylate unit. The MPC monomer has a characteristic feature capable of easily forming a high molecular weight MPC polymer by radical polymerization (Ishihara et al.: Polymer Journal, Vol. 22, pp. 355 (1990)). Therefore, when the polymer film 30 is synthesized from the MPC monomer, it is possible to perform graft bonding of the polymer film 30 with bearing surface 16 under comparatively mild conditions, and to form a large amount of phosphorylcholine groups on the bearing surface 16 by forming the polymer film 30 having higher density.

[Chemical Formula 1]

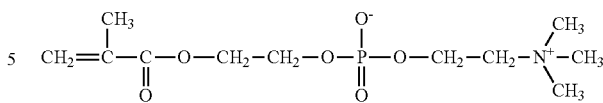

It is also possible to form the polymer film 30 usable in the present invention from not only a homopolymer including a single polymerizable monomer having a phosphorylcholine group, but also a copolymer including a monomer with a phosphorylcholine group and the other vinyl compound monomer, whereby, a function of improving the mechanical strength can be added to the polymer film 30.

(Washing Liquid)

A washing liquid to be used in the production method of the present invention may be those containing an organic solvent and water. In particular, the washing liquid is preferably those prepared by dissolving a surfactant in water. Among radical scavengers, a fat-soluble radical scavenger (for example, vitamin E) can be easily removed by an aqueous solution of the surfactant.

The surfactant may be appropriately selected according to the radical scavenger to be removed, and it is possible to use any surfactants such as a cationic surfactant, an anionic surfactant, a nonionic surfactant, and amphoteric surfactant. When using vitamin E as the radical scavenger, the nonionic surfactant is preferable.

Examples of the surfactant include a nonionic surfactant, a cationic surfactant, an anionic surfactant, and an amphoteric surfactant. In particular, the nonionic surfactant is preferable.

The nonionic surfactant is preferably a polyoxyethylene-based surfactant having a HLB value of 10 to 18 (particularly, HLB value of 13 to 18). It is possible to use, as the polyoxyethylene-based surfactant, polyoxyethylene alkyl ether, polyoxyethylene sorbitan fatty acid ester (Tween 20 (registered trademark)), polyoxyethylene octyl phenyl ether (for example, polyoxyethylene p-t-octyl phenyl ether), polyoxyethylene nonyl phenyl ether (for example, polyoxyethylene p-t-nonyl phenyl ether), and the like. Tween 20 (registered trademark) has high safety to the human body since it is one of food additives, and is suited as a surfactant to be used in the washing liquid.

The nonionic surfactants can be used alone, or two or more thereof can be used in combination. The concentration of the nonionic surfactant may be the concentration which enables removal of the radical scavenger on the substrate surface, and is preferably 0.01 to 10.0% by weight, more preferably 0.1 to 5.0% by weight, still more preferably 0.1 to 1.0% by weight, and particularly preferably 0.3 to 1.0% by weight.

(Light Source for Ultraviolet Irradiation)

It is possible to use, as a light source for irradiation with the ultraviolet-ray (for example, wavelength of 300 to 400 nm), various light sources. It is possible to use, for example, a high-pressure mercury lamp (UVL-400HA, manufactured by Riko-Kagaku Sangyo Co., Ltd.), LED (MeV365-P601JMM, manufactured by Yen electron Volt Co., Ltd.), and the like.

(High Energy Beam Source for Crosslinking Treatment)

It is possible to use, as a high energy beam source to be used in a crosslinking treatment, various source apparatuses. A radiation apparatus can be used, for example, as a gamma-ray source using Co (cobalt) 60 as a radiation source, and an accelerator emitting the electron beam can be used as an electron beam source.

Example 1

In order to examine physical properties of a bearing material (liner 10) of the present application, samples 1a to 1j of the liner 10 for the hip joint replacement shown in FIG. 2 were prepared. Common production conditions of each sample are as follows.

[Step 1] A UHMWPE powder having a molecular weight of about 3,500,000 was mixed with a liquid of vitamin E (α-tocopherol) to prepare a mixed powder. The content of vitamin E was 0.1% by weight based on UHMWPE. The mixed powder was molded by compression molding using a mold to obtain a substrate 12 made of a material containing vitamin E and UHMWPE. The compression molded article obtained was irradiated with the gamma-ray at a dose of 100 kGy and then subjected to a heat treatment at 123° C. for 12 hours, thus performing the crosslinking reaction of PE. A substrate 12 made of a material containing vitamin E and CLPE was obtained by these treatments.

[Step 2] The substrate 12 was immersed in a washing liquid and washed for only a prescribed time while stirring. The washing temperature was set at 70° C.

[Step 3] After washing, the substrate 12 was immersed in an acetone solution (concentration of 10 mg/mL) of benzophenone (photoinduced polymerization initiator) for 30 seconds and immediately pulled up, and then a solvent on a surface of the substrate 12 was removed. In a state where the substrate 12 is immersed in an aqueous MPC solution (concentration of 0.5 mol/L, aqueous solution temperature of 60° C.), a bearing surface 16 of the substrate 12 was irradiated with the ultraviolet-ray (wavelength of 300 to 400 nm) with an intensity of 5.0 mW/cm$^2$ for 90 minutes (1.5 hours) to form a polymer film (MPC polymer film) 30 graft-bonded with the surface of the bearing surface 16.

In the above steps 1 to 3, conditions varying depending on each sample are shown below.

(Sample 1a) Samples were produced without washing of the step 2.

(Sample 1b) In step 2, using an aqueous Tween 20 (registered trademark) solution having the concentration of 1.0% by weight as the washing liquid, washing was performed under the conditions of the washing temperature of 70° C. and the washing time of 3 hours.

(Sample 1c) In step 2, using an aqueous Tween 20 (registered trademark) solution having the concentration of 1.0% by weight as the washing liquid, washing was performed under the conditions of the washing temperature of 70° C. and the washing time of 6 hours.

(Sample 1d) In step 2, using an aqueous Tween 20 (registered trademark) solution having the concentration of 1.0% by weight as the washing liquid, washing was performed under the conditions of the washing temperature of 70° C. and the washing time of 12 hours.

(Sample 1e) In step 2, using an aqueous Tween 20 (registered trademark) solution having the concentration of 1.0% by weight as the washing liquid, washing was performed under the conditions of the washing temperature of 70° C. and the washing time of 24 hours.

(Sample 1f) In step 2, using an aqueous Tween 20 (registered trademark) solution having the concentration of 1.0% by weight as the washing liquid, washing was performed under the conditions of the washing temperature of 70° C. and the washing time of 48 hours.

(Sample 1g) In the step 2, using ethanol as the washing liquid, ultrasonic washing was performed under the conditions of the washing time of 30 minutes.

(Sample 1h) In the step 2, using ethanol as the washing liquid, Soxhlet washing was performed under the conditions of the washing time of 72 minutes.

(Sample 1i) In the step 2, using acetone as the washing liquid, ultrasonic washing was performed under the conditions of the washing time of 30 minutes.

(Sample 1j) In the step 1, a substrate 12 was formed without adding vitamin E and the dose of the gamma-ray was set at 50 kGy. The step 2 was not performed.

(Sample 1k) In the step 1, a substrate 12 was formed without adding vitamin E and the dose of the gamma-ray was set at 50 kGy. The steps 2 and 3 were not performed. Namely, samples were produced without coating the substrate 12 made of CLPE with a polymer film 30.

The washing conditions of samples 1a to 1k in the step 2 are collectively shown in Table 1.

TABLE 1

| Sample No. | Washing liquid Type | Concentration (% by weight) | Washing temperature (° C.) | Washing time (hours) |
|---|---|---|---|---|
| 1a | Without washing | — | — | — |
| 1b | Tween 20 (registered trademark) | 1.0 | 70 | 3 |
| 1c | Tween 20 (registered trademark) | 1.0 | 70 | 6 |
| 1d | Tween 20 (registered trademark) | 1.0 | 70 | 12 |
| 1e | Tween 20 (registered trademark) | 1.0 | 70 | 24 |
| 1f | Tween 20 (registered trademark) | 1.0 | 70 | 48 |
| 1g | Ethanol | Anhydrous | Room temperature | 0.5 |
| 1h | Ethanol | Anhydrous | Room temperature | 72 |
| 1i | Acetone | Anhydrous | Room temperature | 0.5 |
| 1j | Not washed | — | — | — |
| 1k | Not washed | — | — | — |

Abbreviations as used herein have the following meanings.
CLPE: Crosslinked polyethylene
PMPC: Polymer film of MPC
HD-CLPE: High molecular weight polyethylene crosslinked by high dose irradiation
CLPE+E: Material containing vitamin E and crosslinked polyethylene Example 2

(Measurement of Hydrophilicity (Contact Angle with Water))

It is considered that when a polymer film 30 covering a bearing surface 16 of a substrate 12 has high hydrophilicity, affinity with a lubricating liquid is high. The polymer film 30 wetted sufficiently with the lubricating liquid imparts high lubricity to a liner 10, which makes it possible to enhance the wear-resistance of the liner 10. Therefore, the hydrophilicity of the polymer film 30 provided on samples was measured.

Figure 4:
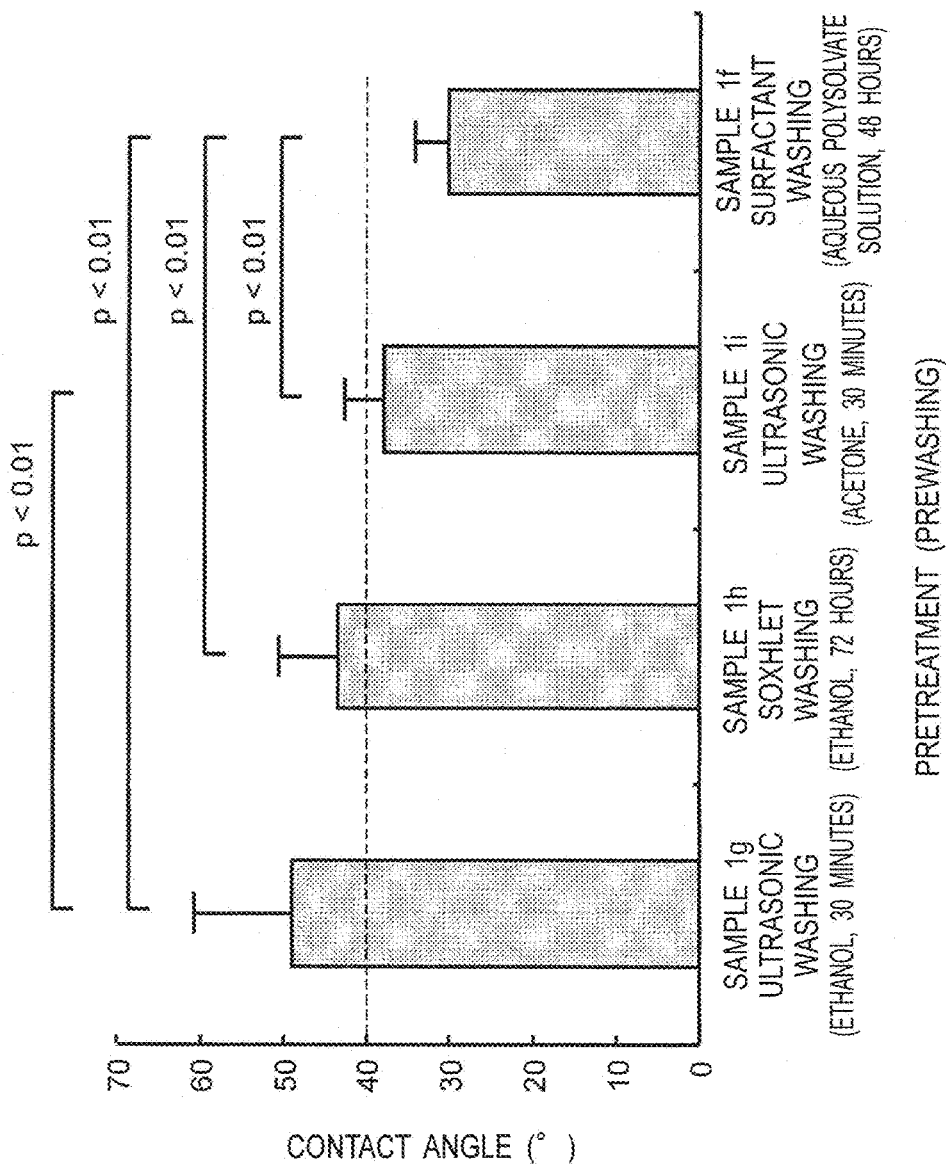
FIG. 4 is a graph showing the measurement results of contact angles with water with respect to samples 1f to 1i measured in Example 2.

With respect to the polymer film 30 provided on samples 1f, 1g, 1h, and 1i, the contact angle with water (static contact angle) was examined. In the measurement, a surface contact angle meter DM300 manufactured by Kyowa Interface Science Co., Ltd. was used and the evaluation was performed by the surface contact angle meter. Using the surface contact angle meter, the static surface contact angle was measured at the time of 60 seconds after dropping 1 μL of pure water droplet on the surface of samples surface in accordance with ISO15989 Standard. The measurement results of the contact angle are shown in FIG. 4.

The contact angle represents the hydrophilicity of the surface of the polymer film 30 formed on the bearing surface 16 of the liner 10. When the contact angle with water is 40° or less, it is judged that a continuous polymer film is formed.

Samples 1g and 1h washed with ethanol exhibited the contact angle of more than 40°. Sample 1i washed with acetone exhibited the contact angle of 40° or less. Sample 1f using Tween 20 as an aqueous nonionic surfactant solution exhibited the lowest contact angle of about 30°. The fact that the contact angle of the polymer film 30 is 40° or less suggests that the polymer film 30 has fewer defects. Therefore, it is found that a polymer film 30 with fewer defects can be formed in samples 1f and 1i.

These results revealed that the aqueous nonionic surfactant solution like Tween 20 is advantageous so as to remove vitamin E from the bearing surface 16 of the substrate 12. Acetone also has high capability of removing vitamin E, but is not suited for use as a bearing material for artificial joint replacement since it may erode PE included in the substrate 12 to cause roughening of the bearing surface 16 in the case of washing for 30 minutes.

Example 3

(Electron Microscope Observation)

Figure 5:
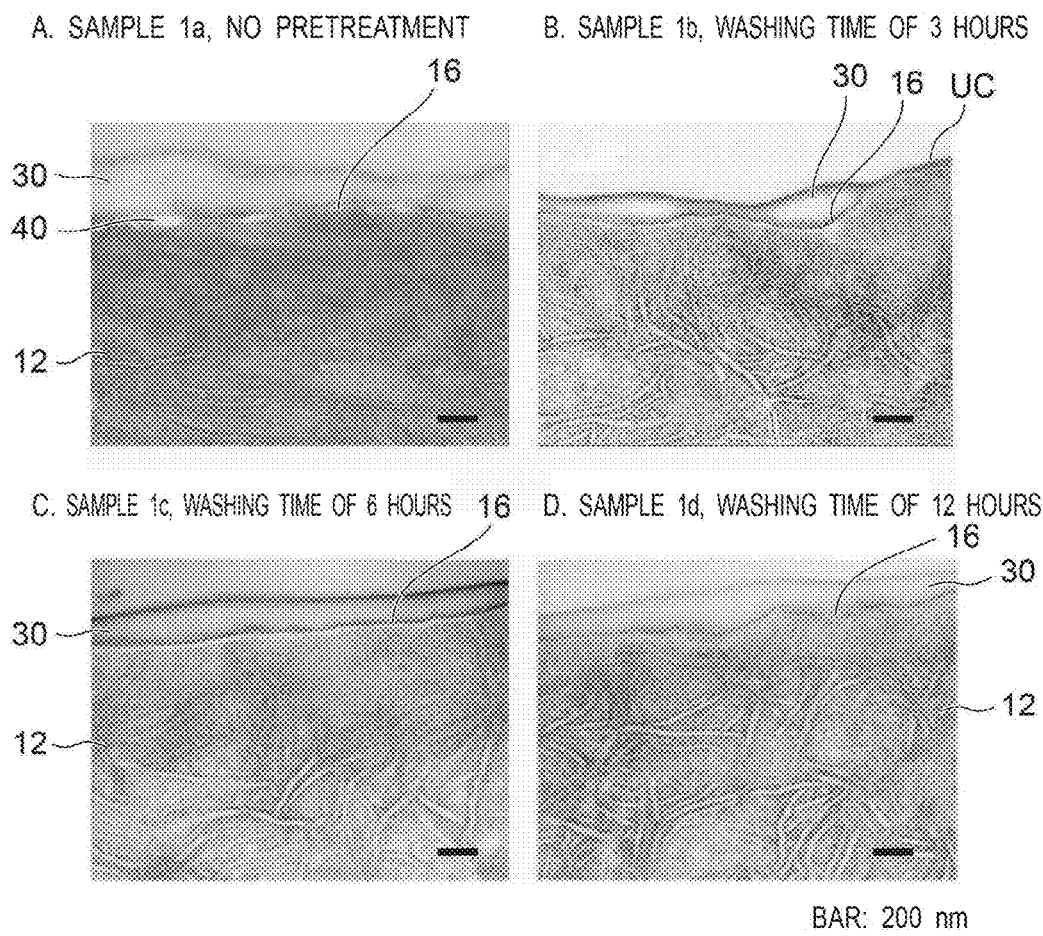
FIGS. 5A to 5D are transmission electron microscope (TEM) images of samples 1a to 1d taken in Example 3.

Cross-sectional TEM images of samples 1a to 1d were observed. Each sample was embedded in an epoxy resin and stained with ruthenium tetrachloride, and then an ultrathin section was cut out using an ultramicrotome to obtain a sample piece. Using TEM (Model JEM-1010, manufactured by JEOL, Ltd.), the sample piece was observed at an accelerating voltage of 100 kV. TEM images of the respective samples are shown in FIG. 5.

In sample 1a (without washing: FIG. 5A), a gap 40 was confirmed between the bearing surface 16 of the substrate 12, and the polymer film 30. In sample 1b (washing time of 3 hours: FIG. 5B), the continuous polymer film 30 was not formed and the uncoated region UC (hole of polymer film 30) remained. In sample 1c (washing time of 6 hours: FIG. 5C) and sample 1d (washing time of 12 hours: FIG. 5D), a polymer film 30 with no defect was formed.

The observation results of the polymer film 30 using TEM images are collectively shown in Table 2. When significant defects (gaps, holes) are confirmed in the polymer film 30, type of the defect was written. When no defect was confirmed, "A" was written.

TABLE 2

| Sample No. | Washing time (hours) | TEM |
|---|---|---|
| 1a | Without washing | Gap |
| 1b | 3 | Hole |
| 1c | 6 | A |
| 1d | 12 | A |

These results revealed that, when using a nonionic surfactant as the washing liquid, it is possible to form a polymer film 30 with fewer defects by washing for 4 hours or more, and more preferably 6 hours or more.

Example 4

(X-Ray Photoelectron Spectroscopy Analysis, Hydrophilicity)

With respect to samples 1a to 1f, a relation between the washing time, and the atom concentration (atom %) of phosphorus and nitrogen atoms of a bearing surface 16 was examined. The atom concentration of phosphorus and nitrogen atoms was measured by XPS analysis. Because of significantly small analysis region of XPS, the measurement results may reflect only local information. Therefore, with respect to one sample, XPS analysis was performed at plural positions (9 positions in the present Example) and an average of the results was determined and regarded as the atom concentration of each sample.

In XPS analysis, using XPS Analyzer (AXIS-HSi165, manufactured by Shimadzu/KRATOS) and using Mg—Kα radiation as an X-ray source, the measurement was performed under the conditions of an applied voltage of 15 kV and a take-off angle of 90°. Using XPS spectra obtained, the atom concentration of phosphorus atom and the atom concentration of nitrogen atom were respectively determined. The atom concentration is expressed by atom % (unit).

Figure 6:
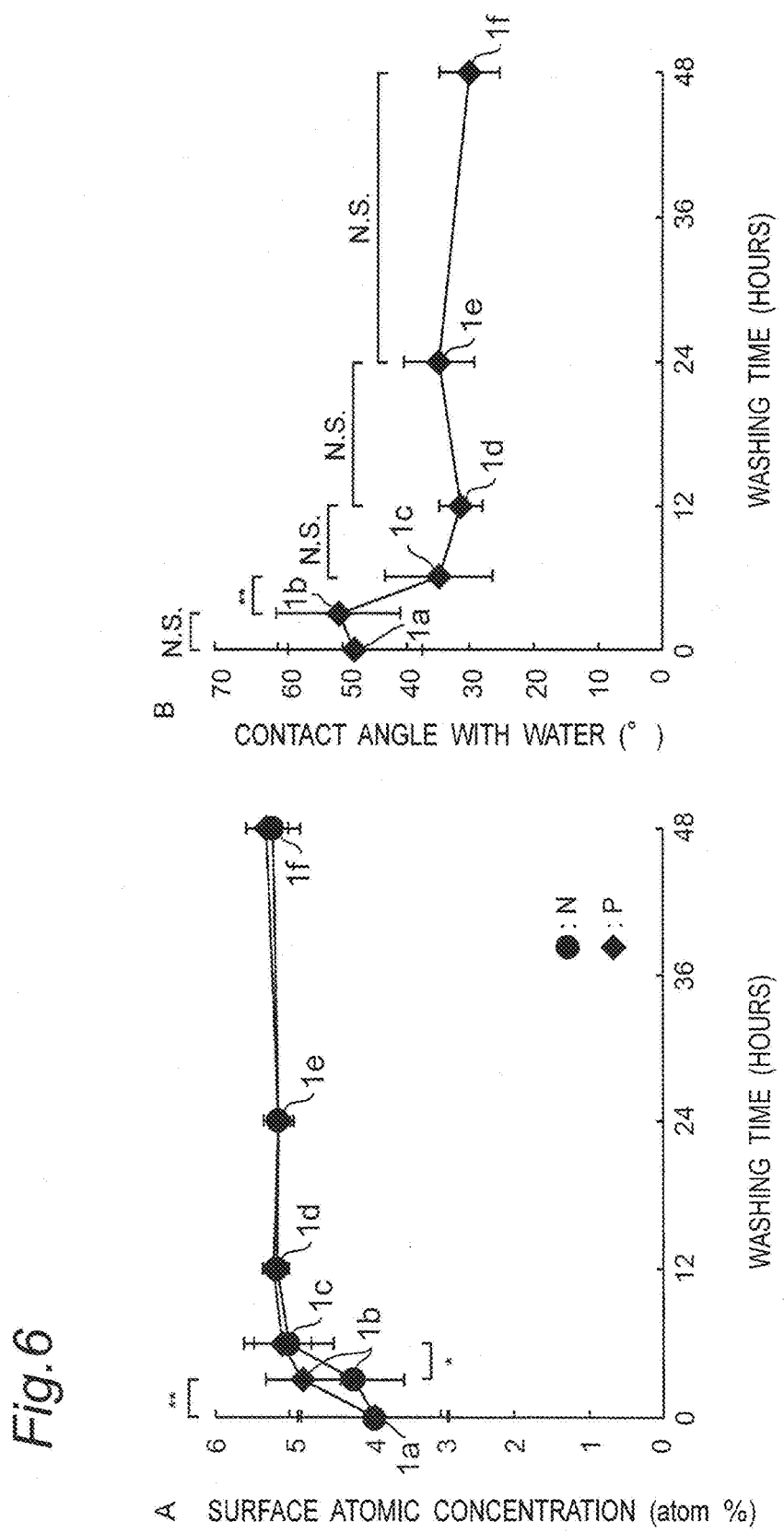
FIG. 6 shows the measurement results of samples 1a to 1f measured in Example 4.

The results of XPS analysis are shown in FIG. 6A. The "contact angles with water" with respect to the same samples 1a to 1f are shown in FIG. 6B.

In sample 1a (without washing), the phosphorus atom concentration of a polymer film 30 was 4.0 atom %, and the nitrogen atom concentration was 4.0 atom %. In sample 1b (washing time of 3 hours), the phosphorus atom concentration of a polymer film 30 was 4.8 atom %, and the nitrogen atom concentration was 4.2 atom %. With respect to samples 1c (washing time of 6 hours) to 1f (washing time of 48 hours), the phosphorus atom concentration was 5.0 to 5.2 atom %, and the nitrogen atom concentration was 5.0 to 5.2 atom %.

It is considered that the polymer film 30 having the phosphorus atom concentration of 3.5 atom % or more and the nitrogen atom concentration of 3.5 atom % or more exhibits comparatively high density. These results reveal that a polymer film having comparatively high density can be formed regardless of the washing time. Because of local measurement of XPS, it should be noted that optimum washing time cannot be judged only from these results.

As shown in FIG. 6B, the contact angle with water is 48° in sample 1a (without washing) and is 51° in sample 1b (washing time of 3 hours), and both contact angles were more than 40°. Meanwhile, the contact angle was 30° to 35° in samples 1c (washing time of 6 hours) to 1f (washing time of 48 hours), and all contact angles were 40° or less.

The fact that the contact angle of the polymer film 30 is 40° or less suggests that the polymer film 30 has fewer defects. These results revealed that the polymer film 30 with fewer defects can be formed when the washing time is 4 hours or more, and preferably 6 hours or more.

It was confirmed from the results of the TEM image in FIG. 5, the atom concentration in FIG. 6A, and the contact angle with water in FIG. 6B that the polymer film 30 having the contact angle with water of 40° or less is a polymer film 30 with fewer defects such as gap 40 and uncoated region UC.

Example 5

(Wear Test 1)

Using sample pieces produced under the conditions of samples 1d, 1j, and 1k, a wear test (pin-on-disk test) was performed. The sample piece used in this wear test was a 3 mm thick flat plate-like specimen, and the method of producing each test piece was the same as in the above-mentioned samples 1d, 1j, and 1k.

Figure 7:
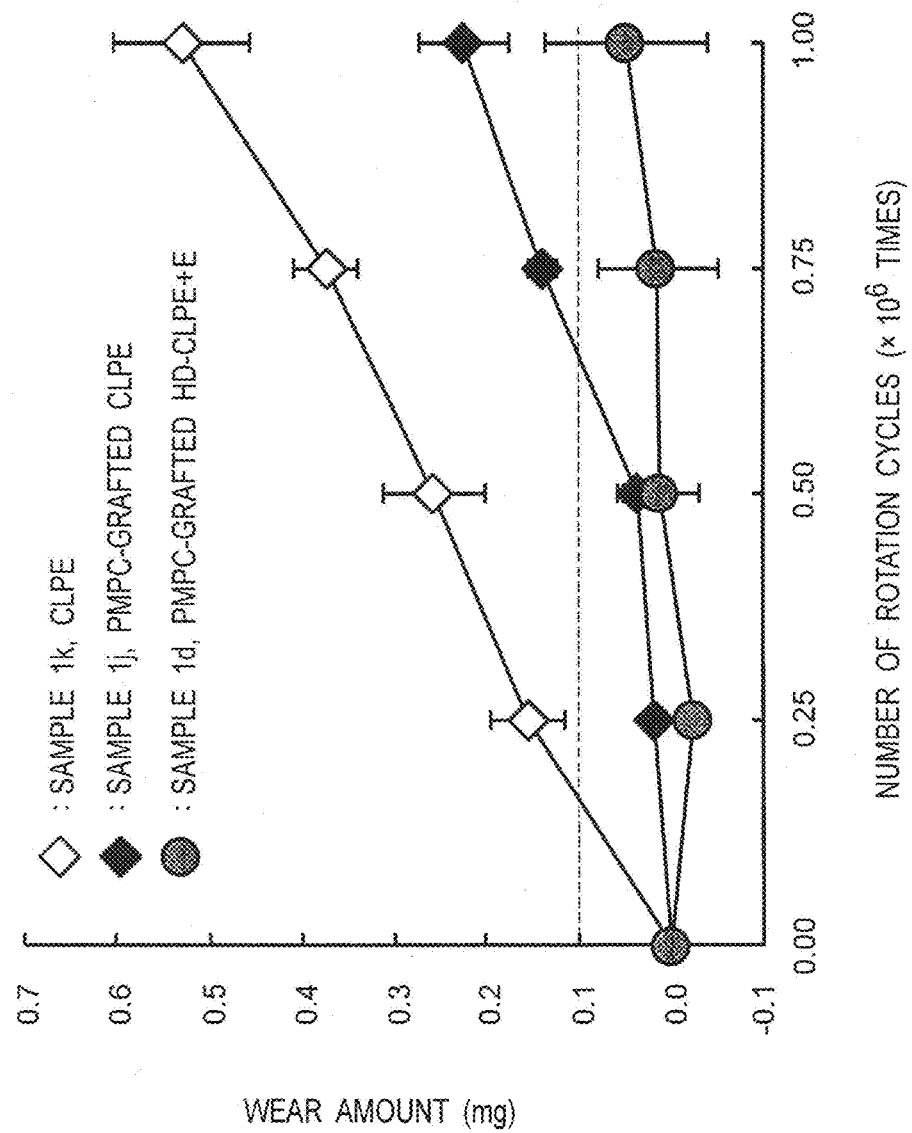
FIG. 7 is a graph showing the results of a wear test 1 of samples 1d, 1j, and 1k performed in Example 5.

With reference to ASTM F732 Standard, using pin-on-disk type wear test apparatus (Ortho-POD, manufactured by AMTI Inc.), a multi-direction sliding test (test on the assumption of the frictional operation which occurs during normal walking in a hip joint) was performed. A cobalt-chromium (Co—Cr) alloy was used as the material of a pin type specimen. The multi-direction sliding test was performed in bovine serum at 37° C. The test was performed under the conditions of a maximum load of 213 N, a sliding distance of 30 mm, and a sliding speed of 1 Hz up to 1,000,000 times ($1\times10^6$ times) and then the amount of wear with time of the disc-shaped specimen of each material was evaluated by a change in weight. The results are shown in FIG. 7.

(Wear Test 2)

A wear test was performed in the environment, which reproduces use conditions in the human body, by artificially bearing samples (a liner for a hip joint replacement) produced under the conditions of samples 1d, 1j, and 1k, and an artificial femoral head. The method of producing each test piece was the same as in the above-mentioned samples 1d, 1j, and 1k.

Figure 8:
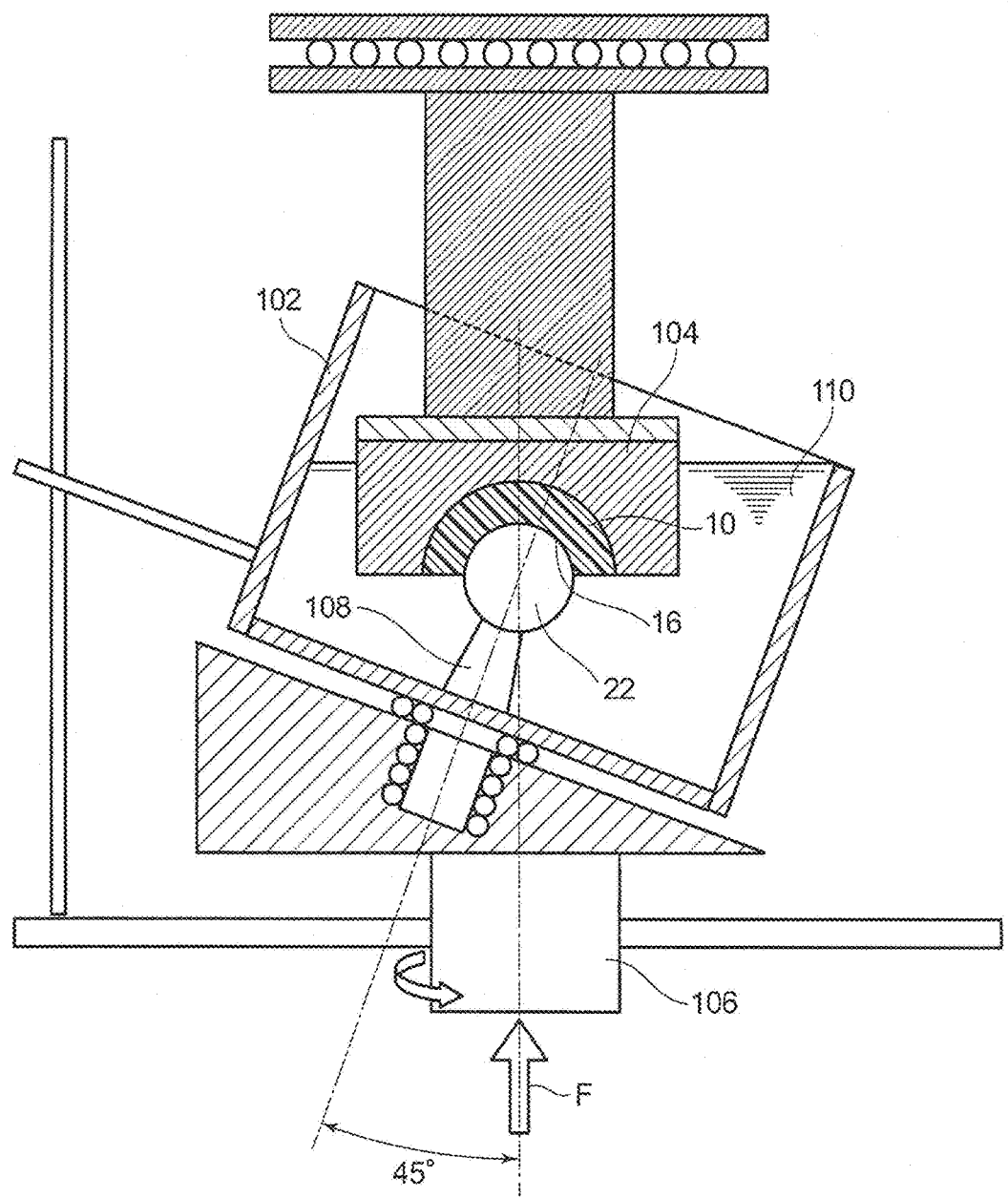
FIG. 8 is a schematic view of a wear test apparatus used in a wear test 2 of Example 5.

In the wear test, a wear test apparatus (manufactured by MTS Ltd.) capable of stimulating the state sliding while the hip joint is swiveling. FIG. 8 is a schematic side view of the wear test apparatus including a container 102 for storing a fluid-like lubricant is fixed to a rotary motor 106 in an inclined state (for example, 45°). A holder 104 for fixing a liner 10 for hip joint replacement is disposed on the upper portion of the container 102. A femoral head fixing shaft 108 with a femoral head fixed at tip is disposed inside the container 102, and can apply a load F to the femoral head 22 in an upward direction in the state where the femoral head 22 is fitted in a bearing surface 16 of the liner 10 for hip joint replacement.

In the wear test, in order to evaluate wear-resistance of the liner 10 for hip joint replacement in the state of stimulating in the living body, the liner 10 for hip joint replacement and the femoral head 22 were immersed in 25% bovine serum 110 containing 0.1% sodium azide and 20 mM ethylenediaminetetraacetic acid trisodium salt. Using a femoral head 22 having a diameter of 26 mm made of a commercially available Co—Cr alloy, walking state was simulated by walking conditions of Double Peak Paul with two peaks of 183 kgf and 280 kgf in one walking cycle per second. The test was performed up to 10,000,000 times ($1\times10^7$ times) and the amount of wear with time of the liner for hip joint replacement of each material was evaluated by a change in weight. The results are shown in FIG. 9.

In the graph of FIG. 9, the wear amount sometimes shows a minus value. This is because the polymer film 30 of the liner for hip joint replacement and the substrate 12 adsorbed moisture, and therefore the weight increased. In this Example, when the wear amount shows the minus value (namely, when the weight increases), it will be regarded that the wear amount was zero.

In FIG. 7 and the following description, a study will be made of the results of wear tests 1 and 2.

It is considered that the bearing material (liner 10) will be replaced when the wear amount reaches 0.1 mg. It is estimated that $1.0\times10^6$ times corresponds to about one year.

In sample 1k formed from CLPE containing no vitamin E, the wear amount reached 0.1 mg at about $0.2\times10^6$ times. In other words, there may be a need for an artificial joint replacement using the liner 10 produced under the conditions of sample 1k to be replaced in a relatively early period.

In sample 1j which is formed from CLPE containing no vitamin E and is provided with a polymer film 30, the wear amount reached 0.1 mg at about $0.7\times10^6$ times. In other words, there may also be a need for an artificial joint replacement using the liner 10 produced under the conditions of sample 1j to be replaced.

In sample 1f which is formed from CLPE containing vitamin E and is provided with a polymer film 30, the wear amount did not reach 0.1 mg even at about $1\times10^6$ times. In other words, there may be no need for an artificial joint replacement using the liner 10 produced under the conditions of sample 1f to be replaced over a long period of time.

Example 6

(Oxidation Test)

Using samples 1d, 1j, and 1k, two types of oxidation tests were performed.

In a first oxidation test, the oxidation induction time was examined. In this test, under the conditions where oxidation is likely to occur (heating in oxidation atmosphere), the time needed to start oxidation is measured.

Figure 10B:
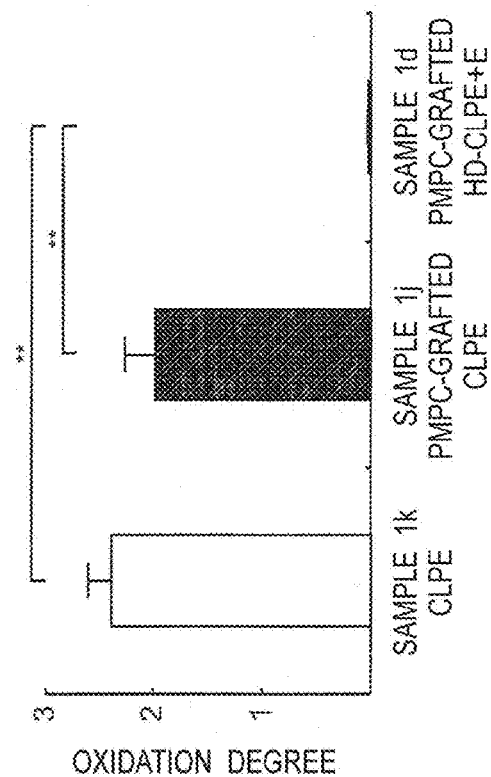
FIGS. 10A and 10B are graphs showing the results of an oxidation test of samples 1d, 1j, and 1k performed in Example 6.
Figure 10A:
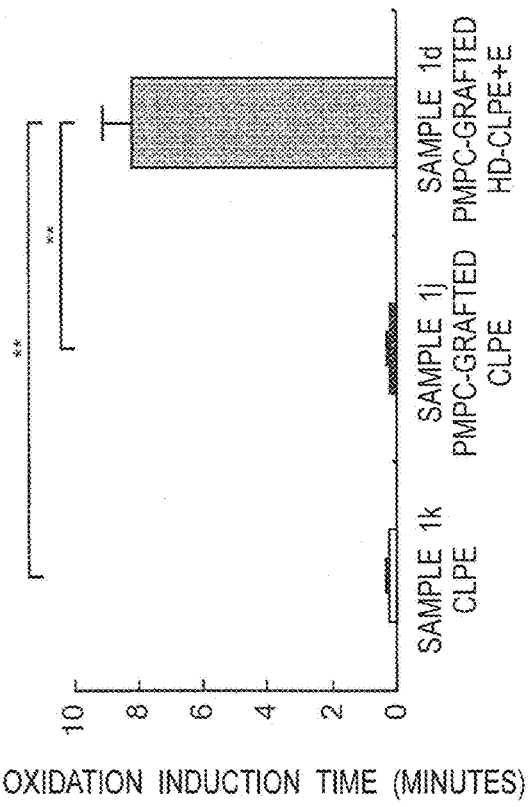

With reference to ASTM D3895 Standard, the time needed to cause the oxidation reaction of each material was measured by differential scanning calorimetry (DSC), and the antioxidant ability was evaluated. After quickly raising the temperature to 200° C. in a nitrogen gas, the atmosphere was replaced by an oxygen gas and then the period between the time at which the atmosphere was replaced and the time at which rising of an exothermic peak due to oxidation occurs was regarded as the oxidation induction time (OIT). The measurement results are shown in FIG. 10A.

In samples 1k and 1j in which the substrate 12 contains no vitamin E, the oxidation reaction started about 10 seconds after starting of the test. Meanwhile, in sample 1d in which the substrate contains vitamin E, the oxidation reaction started after the lapse of about 8 seconds or more since the starting of the test. It was possible to extend the time to the starting of oxidation about 50 times by inclusion of vitamin E.

In a second oxidation test, the degree of oxidation (oxidation degree) was measured. Specifically, with respect to samples 1d, 1j, and 1k oxidized by an acceleration test, the oxidation degree was measured.

With reference to ASTM F2003 Standard, a test piece was stored in atmospheric air at 80° C. for 3 weeks to cause the oxidation reaction acceleratively. With respect to each test piece after the acceleration test, the measurement was performed with reference to ASTM F2102 Standard using Fourier transform infrared microspectroscopy (FT-IR) analysis. Using FT-IR microscopic analyzer (Spectrum BX) manufactured by PerkinElmer, Inc., the measurement was performed by a transmission method under the conditions of the resolution of 4 $cm^{-1}$, the integration time of 100 times, and the wave number of 800 to 4,000 $cm^{-1}$. From the obtained FT-IR spectra, an area of a peak (about 1,360 $cm^{-1}$) attributed to a main chain-$CH_2$— of PE and an area of a peak (about 1,680 to 1,750 $cm^{-1}$) attributed to C=O generated by oxidation were determined, and then the relative oxidation degree (C=O peak area/—CH$_2$-peak area) was calculated from a ratio thereof. The measurement results are shown in FIG. 10B.

In samples 1k and 1j in which the substrate 12 contains no vitamin E, the oxidation degree was 2 to 2.3. Meanwhile, in sample 1d in which the substrate contains vitamin E, the oxidation degree was 0.05 or less. The oxidation degree could be suppressed to about 1/40 by inclusion of vitamin E.

The results of two oxidation tests revealed that a substrate 12 having significantly excellent antioxidant ability can be obtained by inclusion of vitamin E in the substrate 12.

Example 7

(Measurement of Hydrophilicity (Contact Angle with Water))

In order to examine physical properties of a bearing material (liner 10) of the present application, samples 1m to 1r of the liner 10 for hip joint replacement as shown in FIG. 2 were prepared. Common production conditions of each sample are as shown below.

[Step 1] A UHMWPE powder having a molecular weight of about 3,500,000 was mixed with a liquid of vitamin E (α-tocopherol) to prepare a mixed powder. The content of vitamin E was 0.1% by weight based on UHMWPE. The mixed powder was molded by compression molding using a mold to obtain a substrate 12 made of a vitamin E-containing UHMWPE. The compression molded article obtained was irradiated with the gamma-ray at a dose of 100 kGy and then subjected to a heat treatment at 123° C. for 12 hours, thus performing the crosslinking reaction of PE. A substrate 12 made of a vitamin E-containing CLPE was obtained by these treatments.

[Step 2] The substrate 12 was immersed in a washing liquid and washed for a prescribed time while stirring for only for 12 hours.

[Step 3] After washing, the substrate 12 was immersed in an acetone solution (concentration of 10 mg/mL) of benzophenone (photoinduced polymerization initiator) for 30 seconds and immediately pulled up, and then a solvent on a surface of the substrate 12 was removed. In a state where the substrate 12 is immersed in an aqueous MPC solution (concentration of 0.5 mol/L, aqueous solution temperature of 60° C.), a bearing surface 16 of the substrate 12 was irradiated with the ultraviolet-ray (wavelength of 300 to 400 nm) with an intensity of 5.0 mW/cm$^2$ for 90 minutes (1.5 hours) to form a polymer film (MPC polymer film) 30 graft-bonded with the surface of the bearing surface 16.

In the above step 2, conditions varying depending on each sample are shown below.

(Sample 1m) In step 2, using an aqueous Tween 20 (registered trademark) solution having the concentration of 1.0% by weight as the washing liquid, washing was performed under the conditions of the washing temperature of room temperature and the washing time of 12 hours.

(Sample 1n) In step 2, using an aqueous Tween 20 (registered trademark) solution having the concentration of 1.0% by weight as the washing liquid, washing was performed under the conditions of the washing temperature of 40° C. and the washing time of 12 hours.

(Sample 1o) In step 2, using an aqueous Tween 20 (registered trademark) solution having the concentration of 1.0% by weight as the washing liquid, washing was performed under the conditions of the washing temperature of 50° C. and the washing time of 12 hours.

(Sample 1p) In step 2, using an aqueous Tween 20 (registered trademark) solution having the concentration of 1.0% by weight as the washing liquid, washing was performed under the conditions of the washing temperature of 60° C. and the washing time of 12 hours.

(Sample 1q) In step 2, using an aqueous Tween 20 (registered trademark) solution having the concentration of 1.0% by weight as the washing liquid, washing was performed under the conditions of the washing temperature of 70° C. and the washing time of 12 hours.

(Sample 1r) In step 2, using an aqueous Tween 20 (registered trademark) solution having the concentration of 1.0% by weight as the washing liquid, washing was performed under the conditions of the washing temperature of 80° C. and the washing time of 12 hours.

In other words, samples 1m to 1r were produced while changing the temperature of the washing liquid from room temperature to 80° C. The washing conditions of samples 1m to 1r are collectively shown in Table 3 below.

TABLE 3

| Sample No. | Washing liquid | | Washing temperature (° C.) | Washing time (hours) |
| --- | --- | --- | --- | --- |
| | Type | Concentration (% by weight) | | |
| 1m | Tween 20 (registered trademark) | 1.0 | Room temperature | 12 |
| 1n | Tween 20 (registered trademark) | 1.0 | 40 | 12 |
| 1o | Tween 20 (registered trademark) | 1.0 | 50 | 12 |
| 1p | Tween 20 (registered trademark) | 1.0 | 60 | 12 |
| 1q | Tween 20 (registered trademark) | 1.0 | 70 | 12 |
| 1r | Tween 20 (registered trademark) | 1.0 | 80 | 12 |

Figure 11:
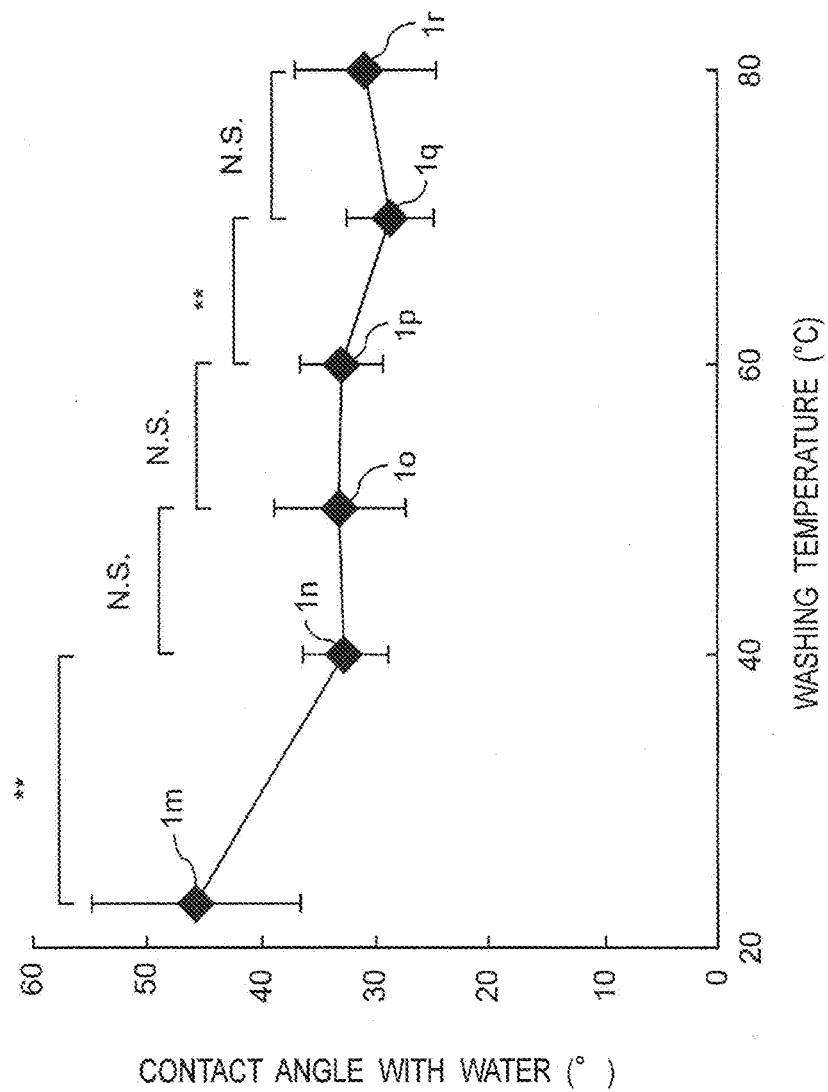
FIG. 11 is a graph showing the measurement results of the contact angle with water with respect to samples 1m to 1r measured in Example 7.

With respect to a polymer film 30 provided on samples 1m to 1r, the contact angle with water (static contact angle) was examined. The results are shown in FIG. 11.

In sample 1m (washing temperature is room temperature), the contact angle was more than 40°. Meanwhile, in samples 1n (washing temperature of 40° C.) to 1r (washing temperature of 80° C.), the contact angle was 40° or less. In particular, the contact angle of samples 1q (washing temperature of 70° C.) and 1r (washing temperature of 80° C.) exhibited significantly low value.

These results revealed that a polymer film 30 with fewer defects can be formed at the washing temperature of 40° C. to 80° C., and a polymer film 30 with still fewer defects can be formed at the washing temperature of 70° C. to 80° C.

Example 8

In order to examine a relation between the ultraviolet-ray irradiation intensity and the physical properties of a bearing material (liner 10), samples 2a to 2h of the liner 10 for hip joint replacement as shown in FIG. 2 were prepared. Common production conditions of each sample are as follows.

[Step 1] A UHMWPE powder having a molecular weight of about 3,500,000 was mixed with a liquid of vitamin E (α-tocopherol) to prepare a mixed powder. The content of vitamin E was 0.1% by weight based on UHMWPE. The mixed powder was molded by compression molding using a mold to obtain a substrate 12 made of a vitamin E-containing UHMWPE. The compression molded article obtained was irradiated with the gamma-ray at a dose of 100 kGy and then subjected to a heat treatment at 123° C. for 12 hours, thus performing the crosslinking reaction of PE. A substrate 12 made of a vitamin E-containing CLPE was obtained by these treatments.

[Step 2] The substrate 12 was immersed in a washing liquid (aqueous Tween 20 (registered trademark) solution having the concentration of 1.0% by weight) and washed for 12 hours while stirring. The washing temperature was set at 70° C.

[Step 3] After washing, the substrate 12 was immersed in an acetone solution (concentration of 10 mg/mL) of benzophenone (photoinduced polymerization initiator) for 30 seconds and immediately pulled up, and then a solvent on a surface of the substrate 12 was removed. In a state where the substrate 12 is immersed in an aqueous MPC solution (concentration of 0.5 mol/L, aqueous solution temperature of 60° C.), a bearing surface 16 of the substrate 12 was irradiated with the ultraviolet-ray (wavelength of 300 to 400 nm) with an intensity of 5.0 mW/cm$^2$ for 90 minutes (1.5 hours) to form a polymer film (MPC polymer film) 30 graft-bonded with the surface of the bearing surface 16.

In the above step 3, the intensity of the ultraviolet-ray was shown in Table 4.

TABLE 4

| Sample No. | Irradiation intensity (mW/cm$^2$) |
|---|---|
| 2a | 0 (Unirradiated) |
| 2b | 1.5 |
| 2c | 3.5 |
| 2d | 5.0 |
| 2e | 7.5 |
| 2f | 10.0 |
| 2g | 15.0 |
| 2h | 20.0 |

Example 9

(Measurement of Hydrophilicity (Contact Angle with Water))

Figure 12:
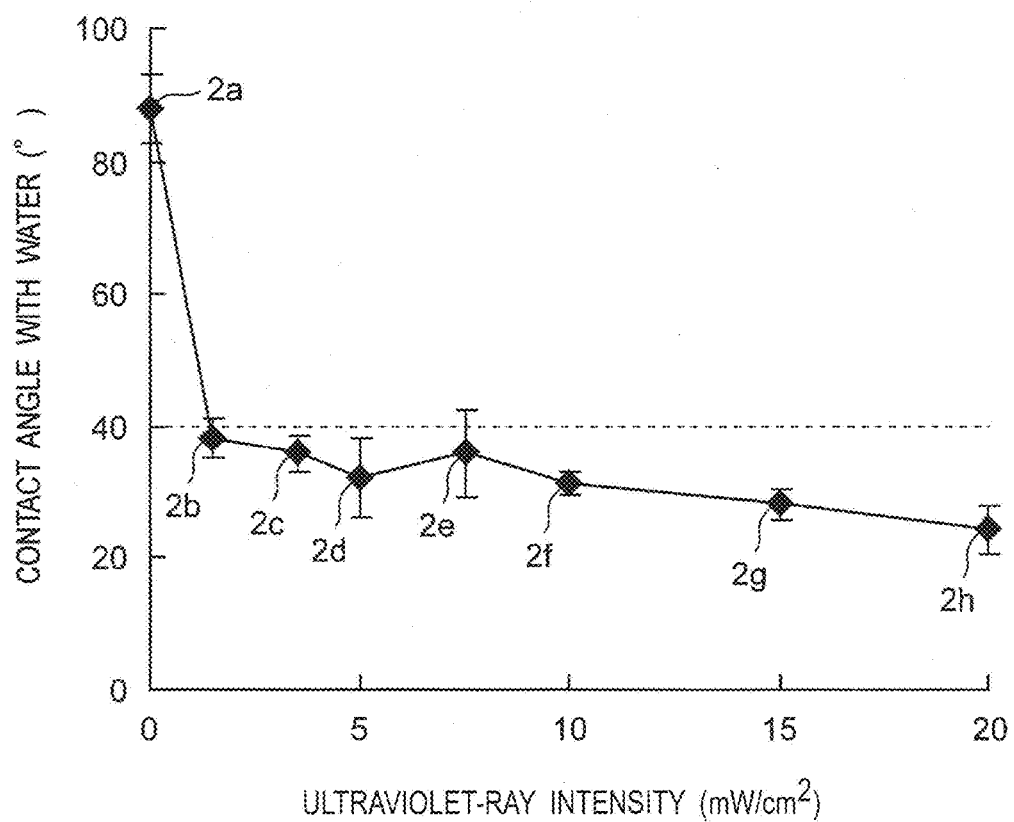
FIG. 12 is a graph showing the measurement results of the contact angle with water with respect to samples 2a to 2h measured in Example 9.

With respect to a polymer film 30 provided on samples 2a to 2h, the contact angle with water (static contact angle) was examined. The measurement conditions were the same as in Example 2. The measurement results are shown in FIG. 12.

In sample 2a unirradiated with the ultraviolet-ray, the contact angle was more than 40°. Meanwhile, in all samples irradiated with the ultraviolet-ray (samples 2b to 2h), the contact angle was 40° or less.

These results revealed that a polymer film 30 with fewer defects can be formed, for example, by irradiating with the ultraviolet-ray at a dose of 0.5 mW/cm$^2$ or more.

Example 10

(Phosphoric Index)

It is considered that the wear-resistance of a liner 10 is enhanced as the density of a polymer film 30 becomes higher.

Here, the "density" of the polymer film 30 is precisely "mass of a polymer chain existing per unit area". However, when the polymer film 30 has sufficiently small film thickness, "density" of the polymer film 30 can be used as an indicator which indicates the density of a polymer chain per unit area. The more, the polymer film 30 has higher density, it is possible to consider that polymer chains exist with high density on a bearing surface 16 of a liner 10.

In this Example, the density of the polymer film 30 was quantitatively defined using a "phosphoric index" as the unit for defining the density of the polymer film.

Here, the "phosphoric index" is defined as an intensity ratio of a peak intensity $I_{phosphate}$ at 1,080 cm$^{-1}$ as an absorption of a phosphate group to a peak intensity $I_{methylene}$ at 1,460 cm$^{-1}$ as an absorption of a methylene group in spectra of FT-IR analysis, namely, $I_{phosphate}/I_{methylene}$.

When a polymer film 30 having a phosphorylcholine group is formed on a substrate 12 containing a polymer material (for example, PE) having a methylene group as a main component, and then FT-IR measurement is performed, a peak of a methylene group attributed to the substrate 12 and a peak of the phosphate group attributed to the polymer film 30 are observed. At this time, when the composition of the substrate 12 is constant and also the film thickness of the polymer film 30 does not extremely change (for example, difference in film thickness within 1 µm), the phosphoric index calculated from two peak intensities is approximately proportional to the number of phosphate groups existing per unit area of the substrate 12.

Patent Documents 4 to 5 disclose the test results about the phosphoric index and durability of the liner 10. Specifically, if the liner 10 has the phosphoric index of 0.28 or more, the durability is noticeably improved as compare with a conventional liner, and the test results of having the durability of 5 years or more could be obtained from an acceleration test. Furthermore, in the liner 10 having the phosphoric index of 0.45 or more, the test results of having the durability of 10 years or more could be obtained. It is possible to say that this durability corresponds to the number of years during which no replacement is needed throughout the lifetime, when the artificial hip joint replacement arthroplasty was performed after reaching an advanced age.

Figure 13:
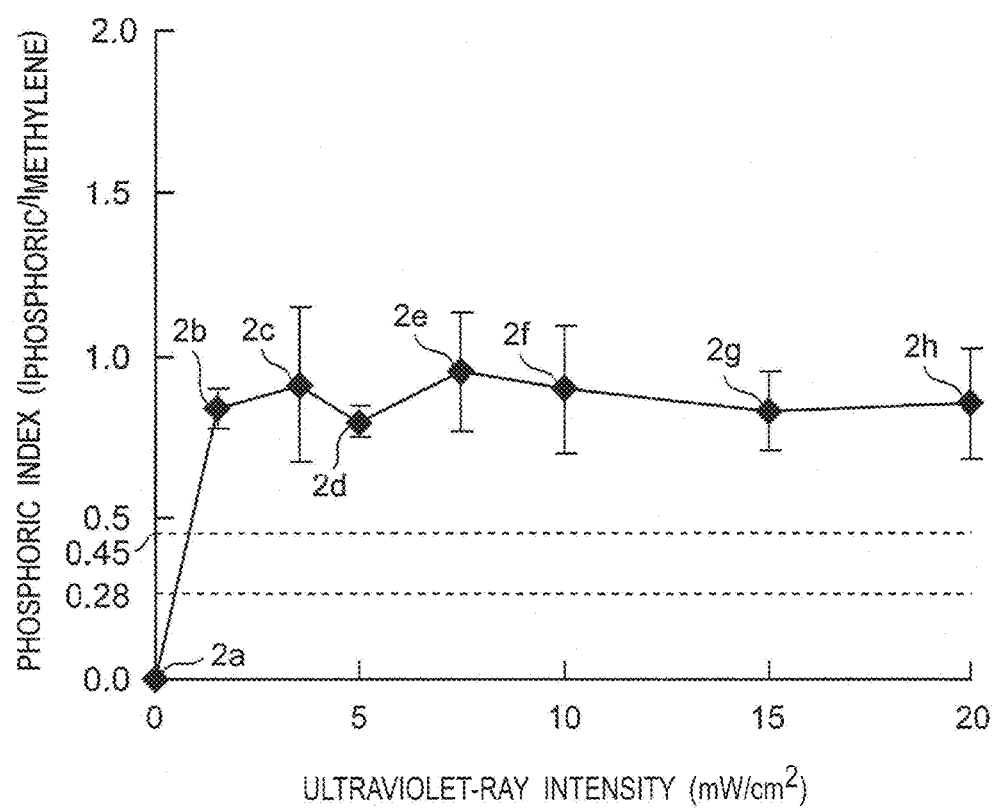
FIG. 13 is a graph showing the measurement results of a phosphoric index with respect to samples 2a to 2h measured in Example 10.

In this Example, with respect to polymer films 30 of samples 2a to 2h, the phosphoric index was determined. Using a FT-IR apparatus FT/IR-6300 type A manufactured by JASCO Corporation, FT-IR measurement was performed under the conditions of the resolution of 4 cm$^{-1}$ and the integration time of 64 times. Next, using Spectra Manager (manufactured by JASCO Corporation), phosphoric acid and methylene groups were quantitatively determined from the obtained spectra, and the phosphoric index was calculated. The phosphoric index of each sample is shown in FIG. 13.

In sample 2a unirradiated with the ultraviolet-ray, the phosphoric index was less than 0.28. Meanwhile, in all samples irradiated with the ultraviolet-ray (samples 2b to 2h), the phosphoric index was 0.45 or more.

These results revealed that a liner 10 having excellent durability (for example, 10 years or more) can be obtained, for example, by irradiating with the ultraviolet-ray at a dose of 0.5 mW/cm$^2$ or more.

Example 11

(Measurement of Film Thickness)

Figure 14:
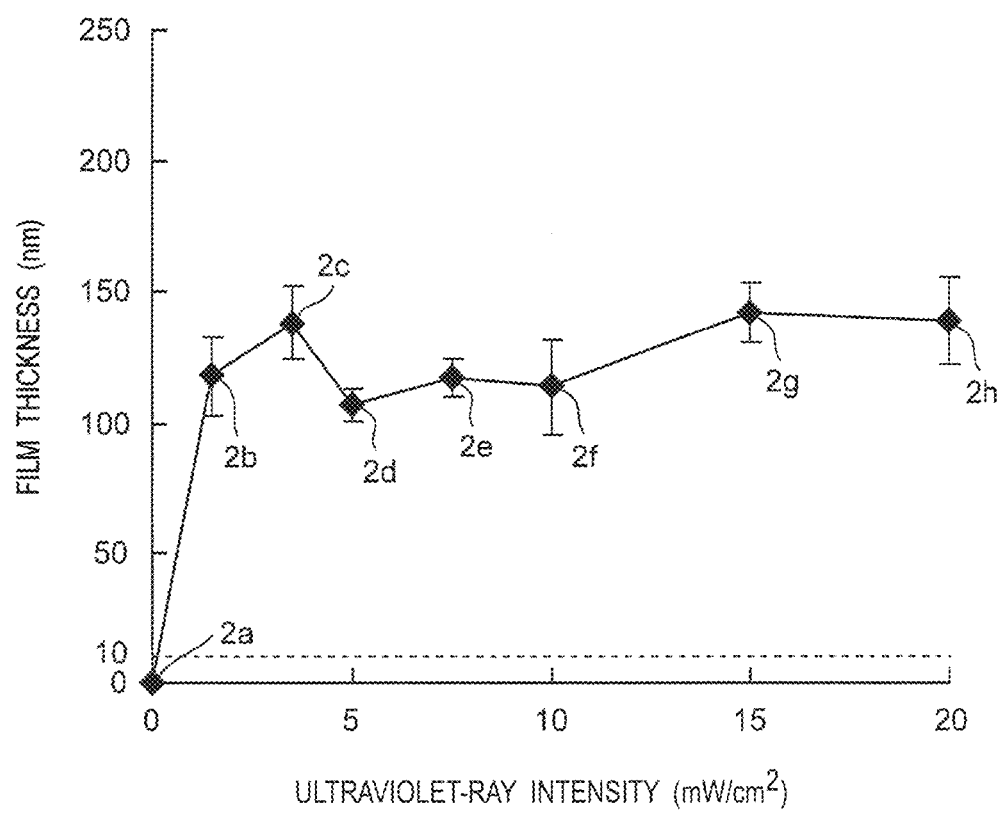
FIG. 14 is a graph showing the measurement results of the film thickness with respect to samples 2a to 2h measured in Example 11.
Figure 17:
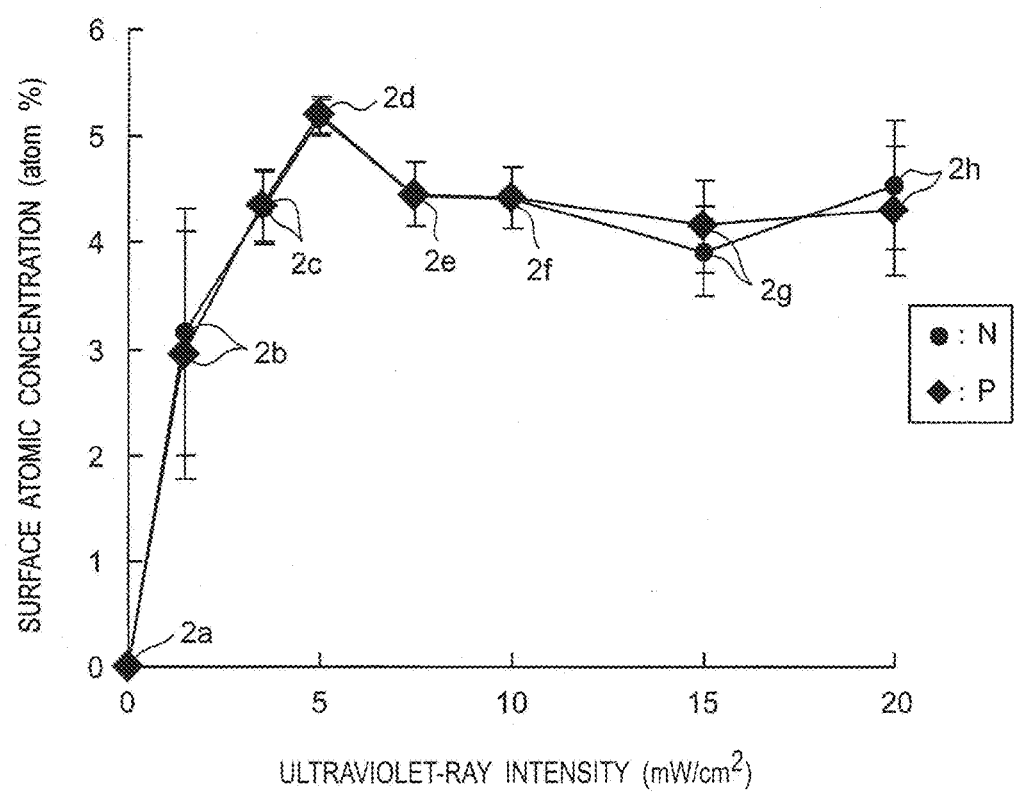
FIG. 17 is a graph showing the measurement results of the surface atom concentration with respect to samples 2a to 2h measured in Example 13.

The film thickness of a polymer film 30 was determined by observing cross-sectional TEM images of samples 2a to 2h. Each sample was embedded in an epoxy resin and stained with ruthenium tetrachloride, and then an ultrathin section was cut out using an ultramicrotome to obtain a sample piece. Using TEM (Model JEM-1010, manufactured by JEOL, Ltd.), the sample piece was observed at an accelerating voltage of 100 kV. From the obtained TEM images, the film thickness (10 points) of the polymer film 30 in the cut face, and the arithmetic average value was calculated. The average film thickness of each sample is shown in FIG. 14.

In sample 2a unirradiated with the ultraviolet-ray, no polymer film 30 was formed. Meanwhile, in all samples irradiated with the ultraviolet-ray (samples 2b to 2h), a polymer film 30 having an average film thickness of 100 nm or more was formed.

These results revealed that a polymer film 30 having a film thickness of 100 nm or more can be formed, for example, by irradiating with the ultraviolet-ray at a dose of 0.5 mW/cm$^2$ or more.

Example 12

Electron Microscope Observation

Cross-sectional TEM images of samples 2a to 2h were observed. The measurement conditions were the same as in Example 3.

TEM images of samples 2b, 2c, 2e, and 2f are shown in FIG. 15 to FIG. 16.

In sample 2b (irradiation intensity of the ultraviolet-ray is 1.5 mW/cm$^2$), sample 2c (irradiation intensity of 3.5 mW/cm$^2$) and sample 2e (irradiation intensity of 7.5 mW/cm$^2$), polymer film 30 with no defect was formed. Meanwhile, in sample 2f (irradiation intensity of 10.0 mW/cm$^2$), a gap 40 was slightly formed between the bearing surface 16 of the substrate 12, and the polymer film 30. However, it is considered to be usable as a liner 10 since this gap 40 is a microgap.

The observation results of a polymer film 30 in TEM images are collectively shown in Table 5. When significant defects (gaps, holes) are confirmed in the polymer film 30, type of the defect was written. When no defect was confirmed, "A" was written. When it was judged to be usable as a liner 10, although slight defects were confirmed in the polymer film 30, "B" was written. In sample 2a, no polymer film 30 was formed since it is unirradiated with the ultraviolet-ray.

TABLE 5

| Sample No. | Irradiation intensity (mW/cm$^2$) | TEM |
| --- | --- | --- |
| 2a | 0 (Unirradiated) | Not formed |
| 2b | 1.5 | A |
| 2c | 3.5 | A |
| 2d | 5.0 | A |
| 2e | 7.5 | A |
| 2f | 10.0 | B (Slight gap) |
| 2g | 15.0 | Gap |
| 2h | 20.0 | Gap |

From these results, it was confirmed that, when the irradiation intensity of the ultraviolet-ray is 0.5 mW/cm$^2$ or more, for example, 1.0 mW/cm$^2$ or more, a continuous polymer film 30 can be formed. When the irradiation intensity is 13.0 mW/cm$^2$ or less, it is possible to suppress a gap between the bearing surface 16 of the liner 10, and the polymer film 30 from generating. In particular, when the irradiation intensity is 9.5 mW/cm$^2$ or less, it was found that a gap capable of being confirmed by TEM is not generated.

Example 13

(X-Ray Photoelectron Spectroscopy Analysis)

With respect to samples 2a to 2h, the atom concentration of phosphorus and nitrogen atoms of a polymer film 30 was measured by XPS analysis. The measurement conditions were the same as in Example 4. The measurement results are shown in FIG. 16.

In sample 2a unirradiated with ultraviolet-ray, the phosphorus atom concentration of a polymer film 30 was 0 atom %, and the nitrogen atom concentration was 0 atom %. In sample 2b (irradiation intensity of the ultraviolet-ray is 1.5 mW/cm$^2$), the phosphorus atom concentration of a polymer film 30 was 2.9 atom %, and the nitrogen atom concentration was 3.1 atom %. In samples 2c (irradiation intensity of 3.5 mW/cm$^2$) to 2h (irradiation intensity 20 mW/cm$^2$), the phosphorus atom concentration was 3.5 atom % or more, and the nitrogen atom concentration was 3.5 atom % or more.

From these results, it is considered that, when the irradiation intensity is 2.0 mW/cm$^2$ or more, a polymer film having comparatively high density can be formed.

Example 14

In order to examine a relation between the ultraviolet-ray irradiation time and the physical properties of a bearing material (liner 10), samples 3a to 3i of the liner 10 for hip joint replacement as shown in FIG. 2 were prepared. Common production conditions of each sample are as follows.

[Step 1] A UHMWPE powder having a molecular weight of about 3,500,000 was mixed with a liquid of vitamin E (α-tocopherol) to prepare a mixed powder. The content of vitamin E was 0.1% by weight based on UHMWPE. The mixed powder was molded by compression molding using a mold to obtain a substrate 12 made of a vitamin E-containing UHMWPE. The compression molded article obtained was irradiated with the gamma-ray at a dose of 100 kGy and then subjected to a heat treatment at 123° C. for 12 hours, thus performing the crosslinking reaction of PE. A substrate 12 made of a vitamin E-containing CLPE was obtained by these treatments.

[Step 2] The substrate 12 was immersed in a washing liquid (aqueous Tween 20 (registered trademark) solution having the concentration of 1.0% by weight) and washed for 12 hours while stirring. The washing temperature was set at 70° C.

[Step 3] After washing, the substrate 12 was immersed in an acetone solution (concentration of 10 mg/mL) of benzophenone (photoinduced polymerization initiator) for 30 seconds and immediately pulled up, and then a solvent on a surface of the substrate 12 was removed. In a state where the substrate 12 is immersed in an aqueous MPC solution (concentration of 0.5 mol/L, aqueous solution temperature of 60° C.), a bearing surface 16 of the substrate 12 was irradiated with the ultraviolet-ray (wavelength of 300 to 400 nm) with an intensity of 5.0 mW/cm$^2$ for a prescribed time to form a polymer film (MPC polymer film) 30 graft-bonded with the surface of the bearing surface 16.

In the above step 3, the irradiation time of the ultraviolet-ray is as shown in Table 6. The unit in the center column is "minutes", and the unit of the right column is "hours".

TABLE 6

| Sample No. | Irradiation intensity (mW/cm$^2$) | Irradiation time (hours) |
| --- | --- | --- |
| 3a | 0 (Unirradiated) | 0 (Unirradiated) |
| 3b | 11 | 0.18 |

TABLE 6-continued

| Sample No. | Irradiation intensity (mW/cm²) | Irradiation time (hours) |
|---|---|---|
| 3c | 15 | 0.25 |
| 3d | 23 | 0.38 |
| 3e | 45 | 0.75 |
| 3f | 60 | 1 |
| 3g | 90 | 1.5 |
| 3h | 120 | 2 |
| 3i | 180 | 3 |

Example 15

(Measurement of Hydrophilicity (Contact Angle with Water))

Figure 18:
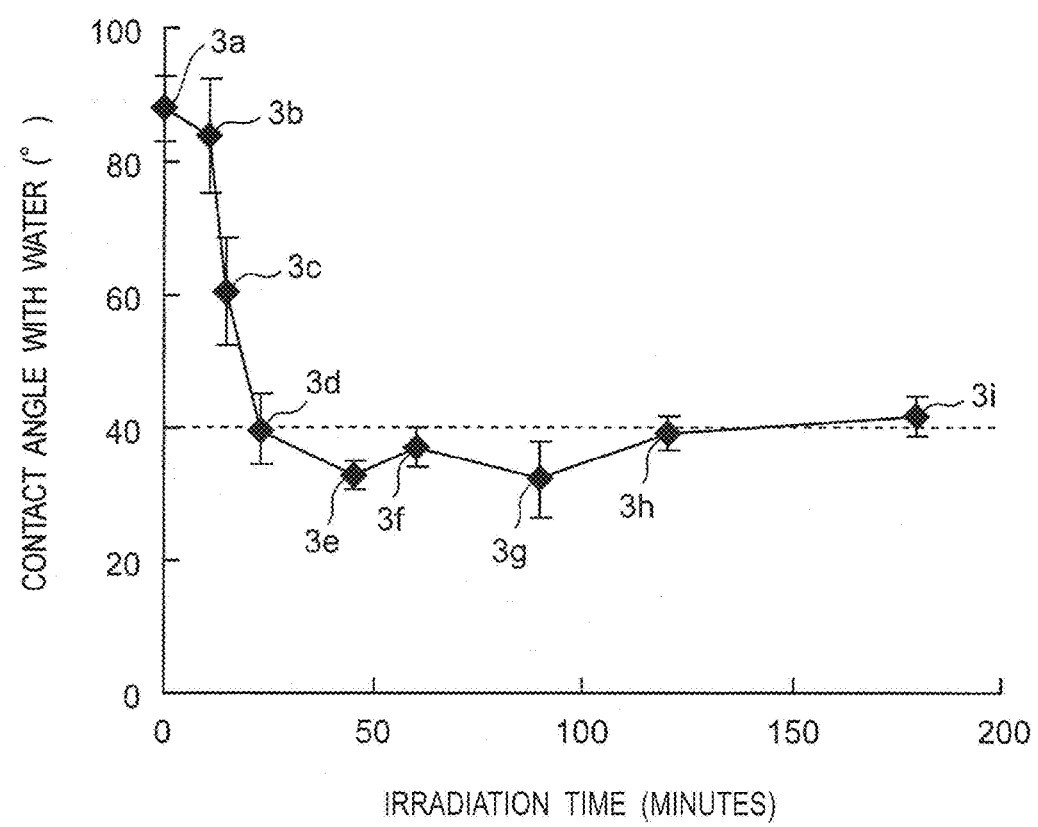
FIG. 18 is a graph showing the measurement results of the contact angle with water with respect to samples 3a to 3i measured in Example 15.

With respect to a polymer film 30 provided on samples 3a to 3i, the contact angle with water (static contact angle) was examined. The measurement conditions are the same as in Example 2. The measurement results are shown in FIG. 18.

In samples 3a (unirradiated with the ultraviolet-ray) to samples 3c (irradiation time of 0.25 hours), the contact angle was more than 40°. Meanwhile, in samples 3d (irradiation time of 0.38 hours) to 3h (irradiation time of 2 hours), the contact angle was 40° or less. In sample 3i (3 hours), the contact angle was 42° and was slightly more than 40°.

These results revealed that, when the irradiation time is 0.3 hours or more, a polymer film 30 with fewer defects can be formed and, in particular, when the irradiation time is 0.3 hours to 2.5 hours, a polymer film 30 with still fewer defects can be formed.

Example 16

(Phosphoric Index)

Figure 19:
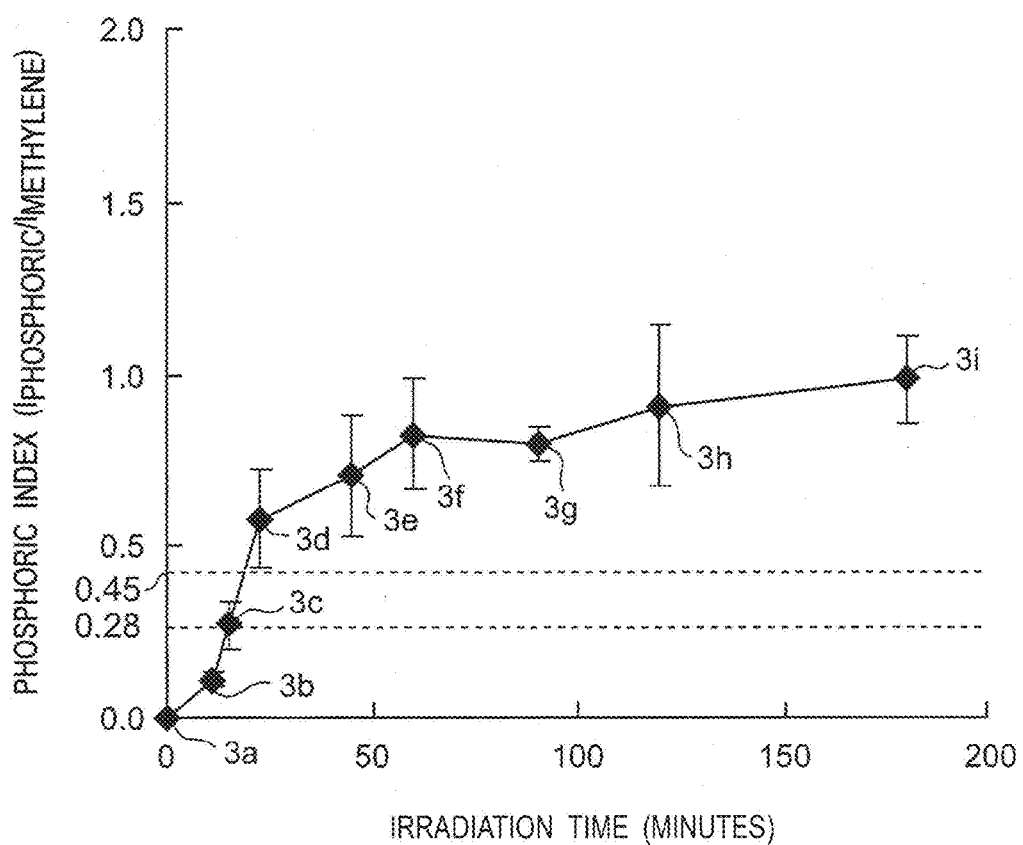
FIG. 19 is a graph showing the measurement results of the phosphoric index with respect to samples 3a to 3i measured in Example 16.

With respect to a polymer film 30 of samples 3a to 3i, the phosphoric index was determined. The measurement conditions were the same as in Example 10. The phosphoric index of each sample is shown in FIG. 19.

In samples 3a (unirradiated with the ultraviolet-ray) to samples 3b (irradiation time of 0.18 hours), the phosphoric index was less than 0.28. In sample 3c (irradiation time of 0.25 hours), the phosphoric index was 0.28 or more and less than 0.45. In samples 3d (irradiation time of 0.38 hours) to 3i (irradiation time of 3 hours), the phosphoric index was 0.45 or more.

These results revealed that, when the irradiation time is 0.3 hours or more, a liner 10 having high durability (for example, 5 years or more) can be obtained and, when the irradiation time is 0.5 hours or more, a liner 10 having excellent durability (for example, 10 years or more) can be obtained.

Example 17

(Measurement of Film Thickness)

Figure 20:
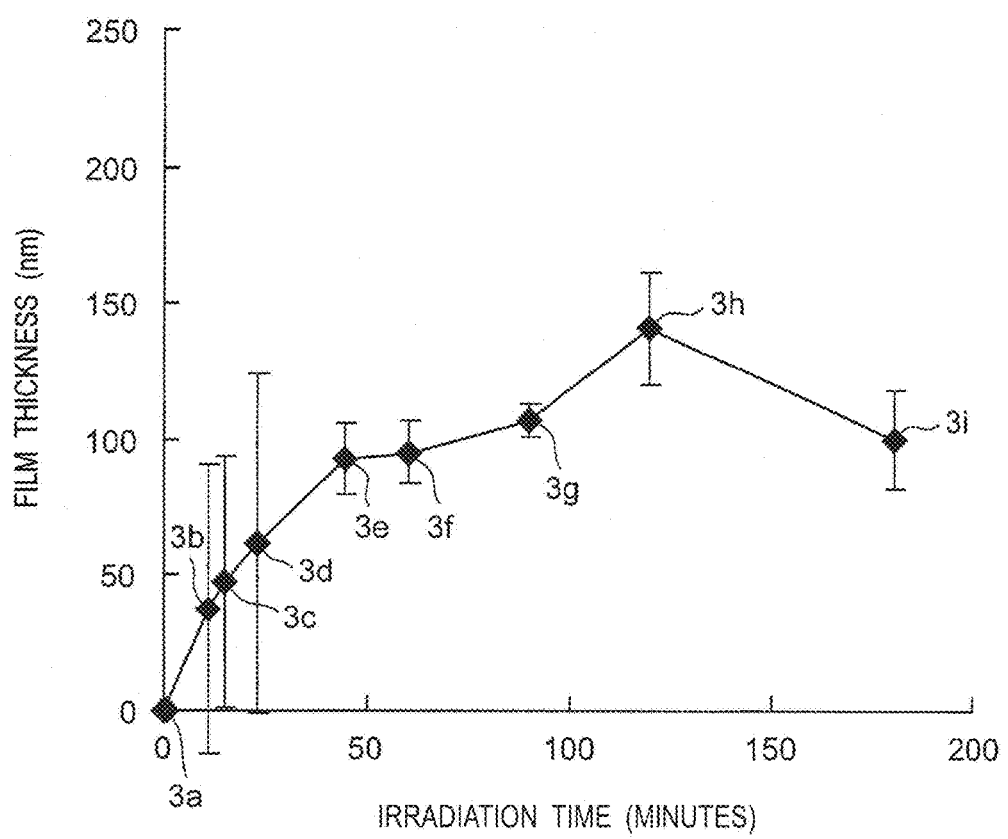
FIG. 20 is a graph showing the measurement results of the film thickness with respect to samples 3a to 3i measured in Example 17.

The film thickness of a polymer film 30 was determined from cross-sectional TEM images of samples 3a to 3i. The measurement conditions were the same as in Example 11. The average film thickness of each sample is shown in FIG. 20.

In sample 3a unirradiated with the ultraviolet-ray, no polymer film 30 was formed. In samples 3b to 3d, the film thickness was 100 nm or less. In samples 3b (irradiation time of 0.18 hours) to 3d (irradiation time of 0.38 hours), holes of a polymer film 30 were observed. In samples 3e (irradiation time of 0.75 hours) to 3f (irradiation time of 1 hour), a continuous polymer film 30 was formed, although the film thickness is 100 nm or less. In samples 3g (irradiation time of 1.5 hours) to 3i (irradiation time of 3 hours), a continuous polymer film 30 having a film thickness of 100 nm or more was formed.

These results revealed that, when the irradiation time is 0.5 hours or more, a continuous polymer film 30 can be formed and, when the irradiation time is 1.2 hours or more, a polymer film 30 having a film thickness of 100 nm or more can be formed.

Example 18

(Electron Microscope Observation)

Cross-sectional TEM images of samples 3a to 3i were observed. The measurement conditions were the same as in Example 3.

TEM images of samples 3d and 3e are shown in FIG. 21.

In samples 3d (irradiation time of 0.38 hours), a continuous polymer film 30 was not be formed, and the uncoated region UC (holes of polymer film 30) was remained. Meanwhile, in sample 3e (irradiation time of 0.75 hours), a polymer film 30 with no defect was formed.

With respect to samples 3a to 3i, the results of TEM images are collectively shown in Table 7. When significant defects (gaps, holes) are confirmed in the polymer film 30, type of the defect was written. When no defect was confirmed, "A" was written. When it was judged to be usable as a liner 10, although slight defects were confirmed in the polymer film 30, "B" was written. In sample 3a, no polymer film 30 was formed since it is unirradiated with the ultraviolet-ray.

TABLE 7

| Sample No. | Irradiation time (hours) | TEM |
|---|---|---|
| 3a | 0 (Unirradiated) | Not formed |
| 3b | 0.18 | Hole |
| 3c | 0.25 | Hole |
| 3d | 0.38 | Hole |
| 3e | 0.75 | A |
| 3f | 1 | A |
| 3g | 1.5 | A |
| 3h | 2 | A |
| 3i | 3 | A |

These results revealed that, when the irradiation time of the ultraviolet-ray is 0.5 hours or more, a polymer film 30 with fewer defects can be formed.

Example 19

(X-Ray Photoelectron Spectroscopy Analysis)

Figure 22:
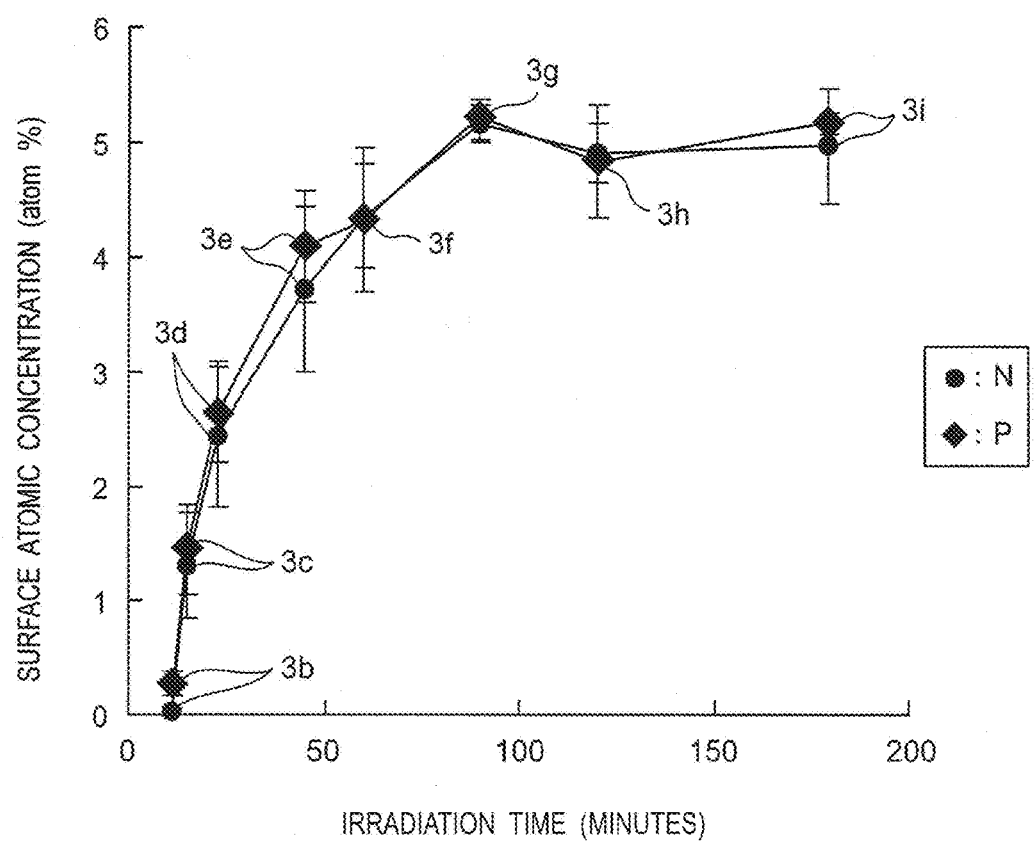
FIG. 22 is a graph showing the measurement results of the surface atom concentration with respect to samples 3a to 3i measured in Example 19.

With respect to samples 3b to 3i, the atom concentration of phosphorus and nitrogen atoms of a polymer film 30 was measured by XPS analysis. The measurement conditions were the same as in Example 4. The measurement results are shown in FIG. 22.

In samples 3b (irradiation time of 0.18 hours) to 3d (irradiation time of 0.38 hours) which include the uncoated region, the phosphorus atom concentration of a polymer film 30 was less than 3.5 atom %, and the nitrogen atom concentration was less than 3.5 atom %. In samples 3e (irradiation time of 0.75 hours) to 3i (3 hours), the phosphorus atom concentration was 3.5 atom % or more, and the nitrogen atom concentration was 3.5 atom % or more.

From these results, when the irradiation time is 0.5 hours or more, a polymer film having comparatively high density can be formed.

Example 20

(Total Energy of the Ultraviolet-Ray)

With respect to samples 1d, 2b, 2c, 2e, 2f, 3d, and 3e, the total energy of the ultraviolet-ray, the contact angle with water, the results of TEM image, and the results of the phosphorus atom concentration are collectively shown in Table 8. Data in the table are arranged in ascending order of the value of the total energy.

When the contact angle with water is 40° or less, "A" was written and, when the contact angle is more than 40°, "C" was written.

Regarding TEM observation, when significant defects (gaps, holes) are confirmed in the polymer film 30, type of the defect was written. When no defect was confirmed, "A" was written. When it was judged to be usable as a liner 10, although slight defects were confirmed in the polymer film 30, "B" was written.

With respect to the results of the phosphorus atom concentration, "C" was written when the phosphorus atom concentration is less than 3.5 atom %, while "A" was written when the phosphorus atom concentration is 3.5 atom % or more.

The results of the contact angle with water revealed that, when the total energy is 6,000 mJ/cm$^2$ or more, a polymer film 30 having excellent hydrophilicity can be formed. Since the contact angle was more than 40° when the total energy is 54,000 mJ/cm$^2$ (Sample 3i), it can be said that the contact angle is more preferably 45,000 mJ/cm$^2$ or less.

The results of TEM images revealed that, when the total energy is 7,000 mJ/cm$^2$ to 70,000 mJ/cm$^2$, a polymer film 30 with fewer defects can be formed. It was also found that, when the total energy is 7,000 mJ/cm$^2$ to 50,000 mJ/cm$^2$, a polymer film 30 with still fewer defects can be formed.

The results of the phosphorus atom concentration revealed that, when the total energy is 10,000 mJ/cm$^2$ or more, it is possible to obtain a polymer film 30 having comparatively high phosphorus atom concentration (3.5 atom % or more).

From the results of the total energy, a study will be made of a relation between the irradiation time and the irradiation intensity.

(1) When the irradiation intensity is 0.5 mW/cm$^2$, the total energy becomes 43,200 mJ/cm$^2$ by setting the irradiation time at 24 hours. This value is within a range of an optimum value of the total energy (7,000 mJ/cm$^2$ to 50,000 mJ/cm$^2$).

(2) When the irradiation energy is 1.0 mW/cm$^2$, the total energy becomes 43,200 mJ/cm$^2$ by setting the irradiation time at 12 hours. This value is within a range of an optimum value of the total energy (7,000 mJ/cm$^2$ to 50,000 mJ/cm$^2$).

TABLE 8

| Sample No. | ultraviolet-ray intensity (mW/cm$^2$) | Irradiation time (hours) | Total energy (mJ/cm$^2$) | Contact angle (°) | TEM | Phosphorus atom concentration (atom %) |
|---|---|---|---|---|---|---|
| 3d | 5 | 0.38 | 6,900 | A | Hole | C |
| 2b | 1.5 | 1.5 | 8,100 | A | A | C |
| 1d | 5 | 1.5 | 27,000 | A | A | A |
| 3e | 5 | 0.75 | 13,500 | A | A | A |
| 2c | 3.5 | 1.5 | 18,900 | A | A | A |
| 2e | 7.5 | 1.5 | 40,500 | A | A | A |
| 3i | 5 | 3 | 54,000 | C | A | A |
| 2f | 10.0 | 1.5 | 54,000 | A | B | A |
| 2g | 15.0 | 1.5 | 81,000 | A | Gap | A |

In sample 3d (total energy of 6,900 mJ/cm$^2$), no continuous polymer film 30 was formed.

In sample 2b (total energy of 8,100 mJ/cm$^2$), a continuous polymer film 30 was formed, but the phosphorus atom concentration was low, for example, less than 3.5 atom %.

In sample 1d (total energy of 27,000 mJ/cm$^2$), sample 3e (total energy of 13,500 mJ/cm$^2$), sample 2c (total energy of 18,900 mJ/cm$^2$), sample 2e (total energy of 40,500 mJ/cm$^2$), and sample 3i (total energy of 54,000 mJ/cm$^2$), a continuous polymer film 30 was formed. The phosphorus atom concentration of the polymer film exhibited comparatively high value, for example, 3.5 atom % or more. In only sample 3i (total energy of 54,000 mJ/cm$^2$), the contact angle with water was more than 40°.

In sample 2f (total energy of 54,000 mJ/cm$^2$), a continuous polymer film 30 was formed, and the phosphorus atom concentration of the polymer film exhibited comparatively high value, for example, 3.5 atom % or more. However, in sample 2f, a gap 40 was slightly formed between a polymer film 30 and a substrate. However, it is considered to be usable as a liner 10 since this gap 40 is a microgap.

In sample 2g (total energy of 81,000 mJ/cm$^2$), no continuous polymer film 30 was formed. The phosphorus atom concentration of the polymer film exhibited comparatively high value, for example, 3.5 atom % or more.

(3) When the irradiation energy is 2.0 mW/cm$^2$, the total energy becomes 43,200 mJ/cm$^2$ by setting the irradiation time at 6 hours. This value is within a range of an optimum value of the total energy (7,000 mJ/cm$^2$ to 50,000 mJ/cm$^2$)

Example 21

In order to examine a relation between the concentration of an aqueous polymerized monomer solution to be used to form a polymer film 30 and the physical properties of a bearing material (liner 10), samples 4a to 4j of the liner 10 for hip joint replacement as shown in FIG. 2 were prepared. Common production conditions of each sample are as follows.

[Step 1] A UHMWPE powder having a molecular weight of about 3,500,000 was mixed with a liquid of vitamin E (α-tocopherol) to prepare a mixed powder. The content of vitamin E was 0.1% by weight based on UHMWPE. The mixed powder was molded by compression molding using a mold to obtain a plate made of a vitamin E-containing UHMWPE. The plate was formed into a bar by machining. The bar obtained was irradiated with the gamma-ray at a dose of 100 kGy and then subjected to a heat treatment at 123° C. for 12 hours, thus performing the crosslinking reaction of PE. After the crosslinking reaction, the bar was machined to obtain a substrate 12 made of a vitamin E-containing CLPE.

[Step 2] The substrate 12 was immersed in a washing liquid (aqueous Tween 20 (registered trademark) solution having the concentration of 1.0% by weight) and washed for 12 hours while stirring. The washing temperature was set at 70° C.

[Step 3] After washing, the substrate 12 was immersed in an acetone solution (concentration of 10 mg/mL) of benzophenone (photoinduced polymerization initiator) for 30 seconds and immediately pulled up, and then a solvent on a surface of the substrate 12 was removed. In a state where the substrate 12 is immersed in an aqueous MPC solution having a prescribed concentration, a bearing surface 16 of the substrate 12 was irradiated with the ultraviolet-ray (wavelength of 300 to 400 nm) with an intensity of 5.0 mW/cm$^2$ for 90 minutes (1.5 hours) to form a polymer film (MPC polymer film) 30 graft-bonded with the surface of the bearing surface 16.

In the above step 3, the concentration of the aqueous MPC solution was shown in Table 9. The "concentration of 0 mol/L" of the aqueous MPC solution used in sample 4a means that water containing no MPC was used.

TABLE 9

| Sample No. | Concentration of aqueous MPC solution (mol/L) |
|---|---|
| 4a | 0 |
| 4b | 0.06 |
| 4c | 0.1 |
| 4d | 0.17 |
| 4e | 0.25 |
| 4f | 0.33 |
| 4g | 0.5 |
| 4h | 0.6 |
| 4i | 0.67 |
| 4j | 1 |

Example 22

(Measurement of Hydrophilicity (Contact Angle with Water))

With respect to a polymer film 30 provided on samples 4a to 4j, the contact angle with water (static contact angle) was examined. The measurement conditions were the same as in Example 2. The measurement results are shown in FIG. 23(a).

Figure 23A:
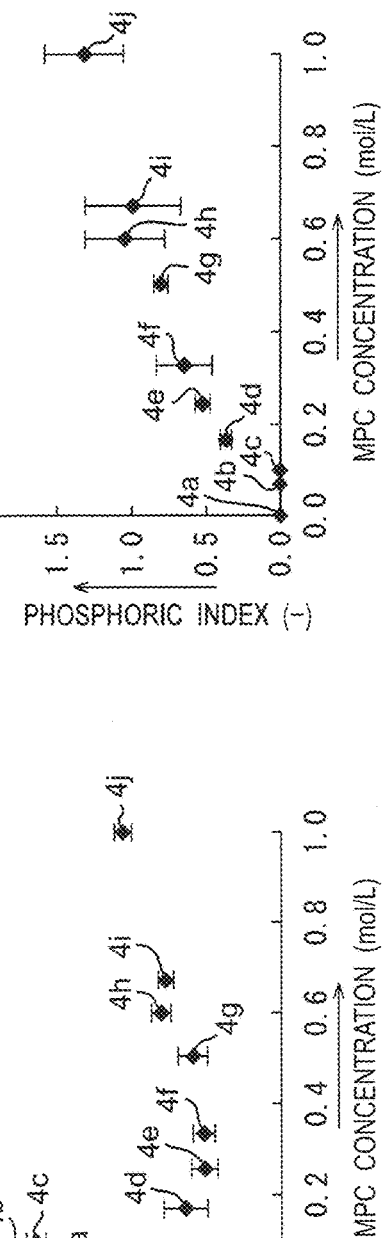
FIG. 23 shows the measurement results of samples 4a to 4j measured in Examples 22 to 25.

As shown in the graph of FIG. 23(a), there was a tendency that the contact angle once increases when the MPC concentration increases (hydrophilization), and increases when the concentration further increases.

In samples 4a (concentration of aqueous MPC solution is 0 mol/L) to samples 4c (concentration of 0.1 mol/L), the contact angle was more than 40°. In samples 4d (concentration of 0.17 mol/L) to 4g (concentration of 0.5 mol/L), the contact angle was 40° or less. In samples 4h (concentration of 0.6 mol/L) to 4i (concentration of 0.65 mol/L), the contact angle was 42° to 44° and was slightly more than 40°. In sample 4j (concentration of 1.0 mol/L), the contact angle was far more than 40°, for example, 58°.

Therefore, in samples 4d (concentration of 0.17 mol/L) to 4i (concentration of 0.65 mol/L), a polymer film 30 with fewer defects can be formed and, in particular, in samples 4d (concentration of 0.17 mol/L) to 4g (concentration of 0.5 mol/L), a polymer film 30 with still fewer defects can be formed.

From these results, it was confirmed that, when the concentration of an aqueous MPC solution is 0.15 mol/L to 0.8 mol/L, a polymer film 30 with fewer defects can be formed and, in particular, when the concentration is 0.15 mol/L to 0.55 mol/L, a polymer film 30 with still fewer defects can be obtained.

Example 23

(Phosphoric Index)

With respect to a polymer film 30 of samples 4a to 4j, the phosphoric index was determined. The measurement conditions were the same as in Example 10. The phosphoric index of each sample is shown in FIG. 23(b).

Figure 23B:
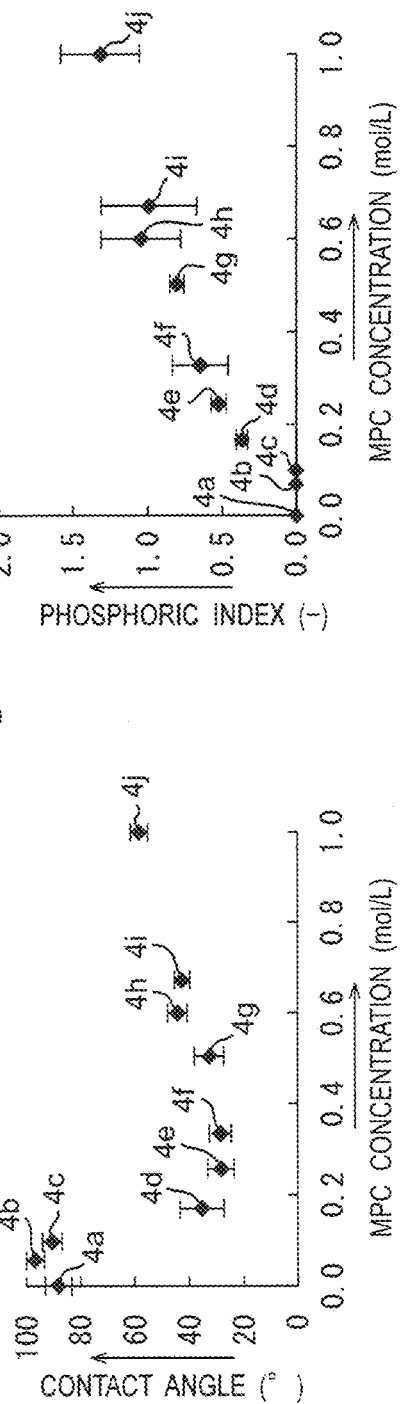

As shown in the graph of FIG. 23(b), if the aqueous MPC solution has the concentration up to 1.0 mol/L, the phosphoric index also increases when the MPC concentration increases. Namely, it is found that the degree of density of MPC in the polymer film increases in proportion to the MPC concentration.

In samples 4a (concentration of aqueous MPC solution of 0 mol/L) to 4c (concentration of 0.1 mol/L), the phosphoric index was less than 0.28. In sample 4d (concentration of 0.17 mol/L), the phosphoric index was 0.28 or more and less than 0.45. In samples 4e (concentration of 0.25 mol/L) to 3j (concentration of 1.0 mol/L), the phosphoric index was 0.45 or more.

These results revealed that, when using an aqueous MPC solution having the concentration of 0.15 mol/L or more, a liner 10 having high durability (for example, 5 years or more) can be obtained and, when using an aqueous MPC solution aqueous MPC solution of 0.2 mol/L or more, a liner 10 having high durability excellent durability (for example, 10 years or more) can be obtained.

Example 24

(Measurement of Film Thickness)

From cross-sectional TEM images of samples 4a to 4j, the film thickness of a polymer film 30 was determined. The measurement conditions were the same as in Example 11. The average film thickness of each sample is shown in FIG. 23(c).

Figure 23C:
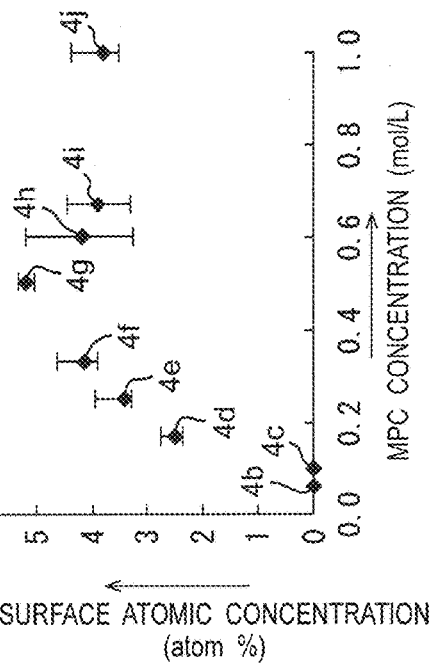

As shown in the graph of FIG. 23(c), if the concentration is up to 1.0 mol/L, the film thickness of the polymer film 30 also increased when the concentration of an aqueous MPC solution increases.

In samples 4a (concentration of an aqueous MPC solution is 0 mol/L) to 4c (concentration of 0.1 mol/L), the film thickness of a polymer film 30 is less than 10 nm, and the polymer film 30 was scarcely formed. In samples 4d (concentration of 0.17 mol/L) to 4f (concentration of 0.33 mol/L), the film thickness was 100 nm or less. In samples 4d (concentration of 0.17 mol/L) and 4e (concentration of 0.25 mol/L), holes of the polymer film 30 were observed. This fact can also be confirmed from that fact that the lower end of the error bar reached the film thickness of 0 nm in FIG. 23(c). In sample 4f (concentration of 0.33 mol/L), the film thickness was 100 nm or less, but a continuous polymer film 30 was formed. In samples 4g (concentration of 0.5 mol/L) to 4j (concentration of 1.0 mol/L), the film thickness was 100 nm or more and also a continuous polymer film 30 was formed.

These results revealed that, when the concentration of the aqueous MPC solution is 0.15 mol/L or more, a polymer film 30 having the film thickness of 10 nm or more can be formed and, when the concentration is 0.27 mol/L or more, it is possible to form a continuous polymer film 30 having the film thickness of 10 nm or more.

Example 25

(X-Ray Photoelectron Spectroscopy Analysis)

With respect to samples 4b to 4j, the atom concentration of phosphorus atom of a polymer film 30 was measured by XPS analysis. The measurement conditions were the same as in Example 4. The measurement results are shown in FIG. 23(d).

Figure 23D:
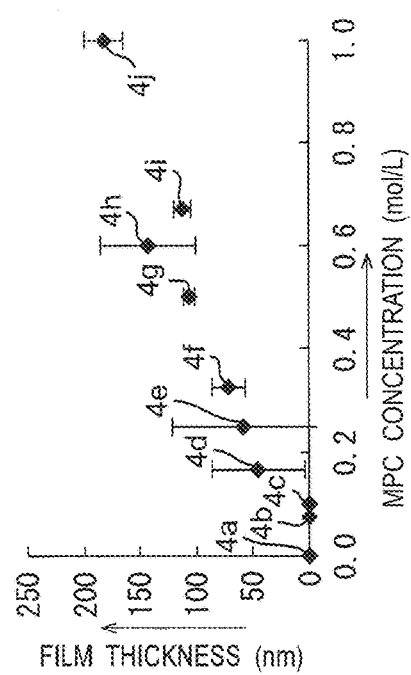

As shown in the graph of FIG. 23(d), there was a tendency that the surface phosphorus atom concentration once increases when the MPC concentration increases, and decreases when the MPC concentration further increases.

In samples 4b (concentration of aqueous MPC solution is 0.06 mol/L) to 4e (concentration of 0.25 mol/L) which include the uncoated region, the phosphorus atom concentration of a polymer film 30 was 3.5 atom % or less. In samples 4f (concentration of 0.33 mol/L) to 4j (concentration of 1.0 mol/L), the phosphorus atom concentration was 3.5 atom % or more. In particular, in samples 4f (concentration of 0.33 mol/L) to 4h (concentration of 0.6 mol/L), the phosphorus atom concentration was 4 atom % or more.

From these results, it is considered that, when the concentration of an aqueous MPC solution is 0.27 mol/L or more, a polymer film having comparatively high density can be formed. In particular, when the concentration is 0.27 mol/L to 0.63 mol/L, it is considered that a polymer film having higher density can be formed.

Example 26

(Electron Microscope Observation)

Cross-sectional TEM images of samples 4a to 4j were observed. The measurement conditions were the same as in Example 3.

TEM images of samples 4e, 4f, 4i, and 4j are shown in FIG. 24.

In sample 4e (concentration of 0.25 mol/L), a continuous polymer film 30 was not formed, and the uncoated region UC (hole of polymer film 30) was remained. In samples 4f (concentration of 0.33 mol/L) and 4i (concentration of 0.67 mol/L), a polymer film 30 with no defect was formed. In sample 4j (concentration of 1.0 mol/L), a gap 40 was slightly formed between a polymer film 30 and a substrate. However, it is considered to be usable as a liner 10 since this gap 40 is a microgap.

With respect to samples 4a to 4j, the results of TEM images are collectively shown in Table 10. When significant defects (gaps, holes) are confirmed in the polymer film 30, type of the defect was written. When no defect was confirmed, "A" was written. When it was judged to be usable as a liner 10, although slight defects were confirmed in the polymer film 30, "B" was written. In sample 4a, no polymer film 30 was formed since water was used in place of an aqueous MPC solution.

TABLE 10

| Sample No. | Concentration of aqueous MPC solution (mol/L) | TEM |
| --- | --- | --- |
| 4a | 0 | Not formed |
| 4b | 0.06 | Not formed |
| 4c | 0.1 | Not formed |
| 4d | 0.17 | Hole |
| 4e | 0.25 | Hole |

TABLE 10-continued

| Sample No. | Concentration of aqueous MPC solution (mol/L) | TEM |
| --- | --- | --- |
| 4f | 0.33 | A |
| 4g | 0.5 | A |
| 4h | 0.6 | A |
| 4i | 0.67 | A |
| 4j | 1 | B |

From these results, it was confirmed that, when the concentration of the aqueous MPC solution is 0.27 mol or more, a continuous polymer film 30 can be formed. When the concentration is 1.0 mol/L or less, it is possible to suppress a gap from generating between a bearing surface 16 and a polymer film 30. In particular, when the concentration is 0.8 mol/L or less, it was found that a gap capable of being confirmed by TEM is not generated.

According to the bearing material according to the present invention (liner 10), a polymer film 30 formed on a bearing surface 16 of a liner 10 exhibits a contact angle with water of 40° or less, and therefore the polymer film 30 has fewer defects such as hole. Therefore, partial wear of the liner 10 due to defects of the polymer film 30 is less likely to occur, which makes it possible to obtain a liner 10 with long lifetime.

According to the method of producing a bearing material according to the present invention (liner 10), it is possible to form a polymer film 30 with fewer defects such as hole and gap on a bearing surface 16 by including the step of washing at least a part (bearing surface 16) of the substrate 12 with a washing liquid before formation of the polymer film 30. Therefore, partial wear of the liner 10 due to defects of the polymer film 30 is less likely to occur, which makes it possible to obtain a liner 10 with long lifetime.

Since any bearing material obtained by the bearing material according to the present invention and the production method of the present invention has long lifetime, it is possible to produce an artificial joint replacement which needs no replacement, or an artificial joint replacement capable of reducing the time of replacement by forming an artificial joint replacement using this bearing material.

INDUSTRIAL APPLICABILITY

The present invention can provide an artificial joint replacement which can be applied to not only the artificial hip joint replacement mentioned in the embodiments, but also various artificial joint replacements such as an artificial spinal, an artificial shoulder joint replacement, an artificial knee joint replacement, an artificial elbow joint replacement, an artificial foot joint replacement, and an artificial finger joint replacement, and which has noticeably improved lifetime.

DESCRIPTION OF REFERENCE NUMERALS

1: Artificial hip joint replacement, 10: Liner, 12: Substrate, 16: Bearing surface, 20: Femoral stem, 22: Femoral head, 30: Polymer film, 40: Gap, and UC: Uncoated region

The invention claimed is:
1. A method of producing a bearing material comprising:
   molding a substrate comprising 0.1% vitamin E by weight based on ultrahigh molecular weight polyethylene (UHMWPE);

washing at least a part of a surface of the substrate by immersing the substrate in a washing liquid at 40° C. to 80° C. for 6 hours or more; and fixing a polymer chain having a phosphorylcholine group at at least the part of the surface by a graft bond after washing so as to form a non-defective polymer film on at least the part of the surface.

2. The method according to claim 1, wherein the washing liquid is an aqueous solution containing a surfactant.

3. The method according to claim 2, wherein the surfactant is a nonionic surfactant.

4. The method according to claim 1, wherein in the washing step, at least a part of the surface is washed at 70° C. to 80° C. for 12 hours or more.

5. The method according to claim 1 further comprising preparing a substrate material, before the step of molding the substrate, wherein the step of preparing the substrate material comprises mixing a powder of the UHMWPE with the vitamin E, and subjecting the obtained the mixed powder to compression molding to obtain the substrate material comprising the 0.1% vitamin E by weight based on UHMWPE.

6. The method according to claim 1, wherein the step of forming the non-defective polymer film comprises irradiating at least the part of the surface with the ultraviolet-ray of an intensity of 0.5 mW/cm$^2$ or more while the part of the surface is in contact with a polymerizable monomer having the phosphorylcholine group.

7. The method according to claim 6, wherein the intensity of the ultraviolet-ray is from 1.0 mW/cm$^2$ to 13 mW/cm$^2$.

8. The method according to claim 6, wherein total energy of the irradiated the ultraviolet-ray is from 6,000 mJ/cm$^2$ to 70,000 mJ/cm$^2$.

9. The method according to claim 6, wherein the irradiation time of the ultraviolet-ray is from 0.5 hours to 24 hours.

10. The method according to claim 1, wherein the step of forming the non-defective polymer film comprises irradiating at least the part of the surface of the substrate with the ultraviolet-ray while at least the part of the surface is immersed in an aqueous solution containing a polymerizable monomer having the phosphorylcholine group, and the concentration of the polymerizable monomer in the aqueous solution is 0.15 mol/L to 1.0 mol/L.

11. The method according to claim 10, wherein the concentration of the polymerizable monomer in the aqueous solution is 0.27 mol/L to 1.0 mol/L.

12. The method according to claim 6, wherein the step of forming the non-defective polymer film further comprises applying a photoinduced polymerization initiator to at least the part of the surface before irradiating with the ultraviolet-ray, and the photoinduced polymerization initiator is excited by the irradiated ultraviolet-ray.

13. The method according to claim 1, wherein the UHMWPE has a molecular weight of $3 \times 10^6$ g/mol or more.

14. The method according to claim 13, further comprising crosslinking the UHMWPE before the step of washing.

* * * * *